US012569635B2

(12) United States Patent
Koerber et al.

(10) Patent No.: US 12,569,635 B2
(45) Date of Patent: Mar. 10, 2026

(54) SYSTEMS AND METHODS FOR CONTROLLING PRESSURE SUPPORT DEVICES

(71) Applicant: KONINKLIJKE PHILIPS N.V., Eindhoven (NL)

(72) Inventors: Achim Koerber, Eindhoven (NL); Tamara Mathea Elisabeth Nijsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 571 days.

(21) Appl. No.: 18/113,234

(22) Filed: Feb. 23, 2023

(65) Prior Publication Data

US 2023/0398319 A1      Dec. 14, 2023

Related U.S. Application Data

(60) Provisional application No. 63/350,438, filed on Jun. 9, 2022.

(51) Int. Cl.
*A61M 16/00*          (2006.01)

(52) U.S. Cl.
CPC ...... *A61M 16/026* (2017.08); *A61M 16/0009* (2014.02); *A61M 2016/0027* (2013.01); *A61M 2230/40* (2013.01)

(58) Field of Classification Search
CPC ... A61M 16/026; A61M 16/009; A61M 16/12
See application file for complete search history.

(56) References Cited

U.S. PATENT DOCUMENTS

| | | | |
|---|---|---|---|
| 9,132,250 B2 | 9/2015 | Allum | |
| 2005/0087190 A1 | 4/2005 | Jafari | |
| 2013/0085425 A1* | 4/2013 | Monsieurs | A61M 16/0051 |
| | | | 128/204.23 |
| 2013/0087146 A1 | 4/2013 | Callaghan | |
| 2014/0034054 A1 | 2/2014 | Angelico | |
| 2014/0116439 A1* | 5/2014 | Troili | A61M 16/0057 |
| | | | 128/204.23 |
| 2021/0016035 A1 | 1/2021 | Euliano | |
| 2021/0093816 A1 | 4/2021 | Liu | |
| 2021/0093824 A1 | 4/2021 | Colefax | |
| 2021/0145308 A1* | 5/2021 | Glenn | G16H 40/63 |
| 2022/0265944 A1 | 8/2022 | Mulqueeny | |
| 2022/0339378 A1* | 10/2022 | LaTorraca | A61M 16/0003 |

OTHER PUBLICATIONS

International Search Report for PCT/EP2023/064915 filed Jun. 5, 2023.

* cited by examiner

*Primary Examiner* — Margaret M Luarca
(74) *Attorney, Agent, or Firm* — Daniel H. Brean

(57)          ABSTRACT

The present disclosure relates to systems and method of controlling the pressure level of a gas mixture being delivered to a patient via a pressure support device adapted to provide breathing support to a patient that varies with time. More specifically, the systems and methods described herein enable the accurate detection of active inspiration by the patient and the fast triggering of an increased inspiratory positive airway pressure pulse. Further, the systems and methods described rely upon the patient pressure measured along a turbulent gas flow path and finds particular application when the pressure support device is configured to provide a non-zero positive end-expiratory pressure.

4 Claims, 26 Drawing Sheets

Figure 25A:
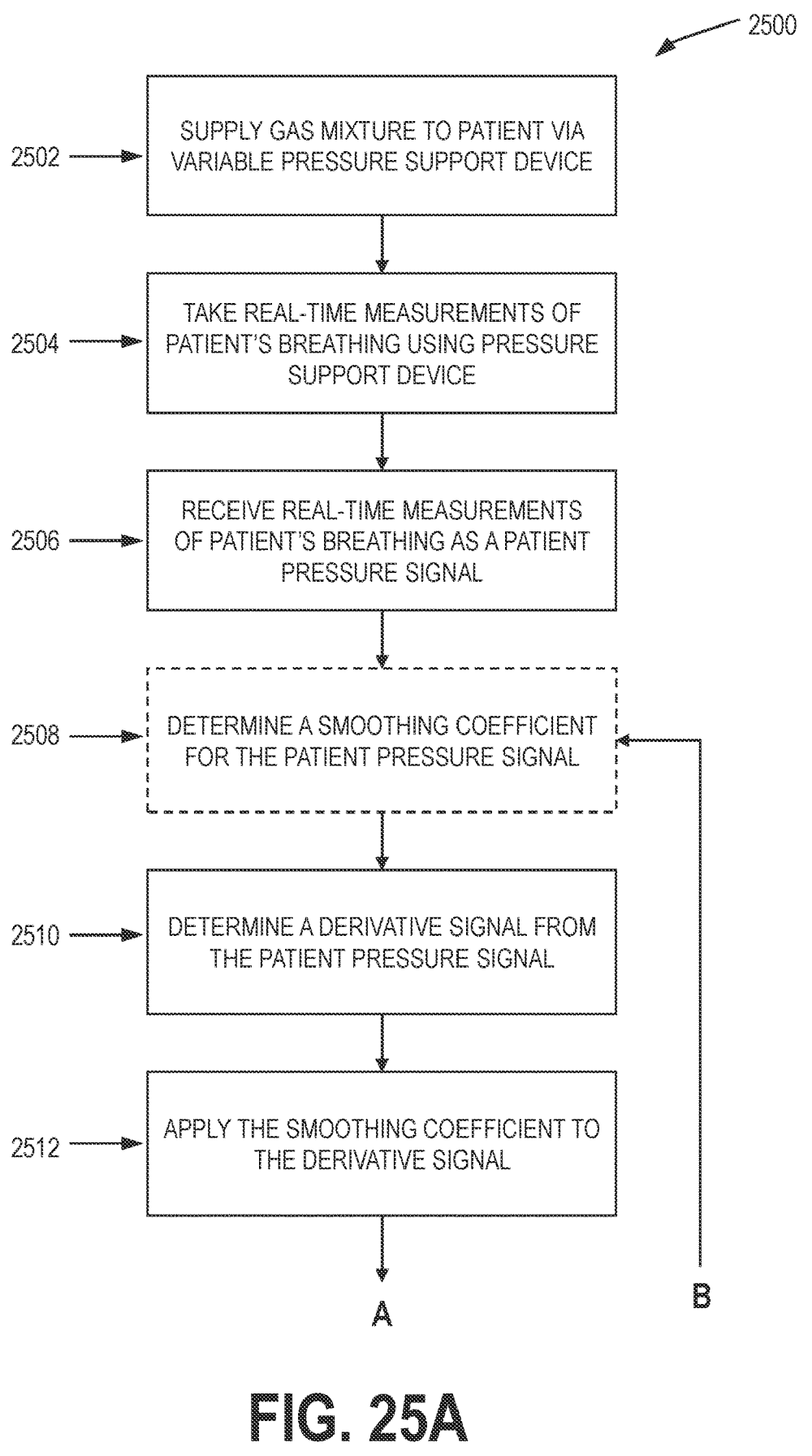

2500

2502 → SUPPLY GAS MIXTURE TO PATIENT VIA VARIABLE PRESSURE SUPPORT DEVICE

2504 → TAKE REAL-TIME MEASUREMENTS OF PATIENT'S BREATHING USING PRESSURE SUPPORT DEVICE

2506 → RECEIVE REAL-TIME MEASUREMENTS OF PATIENT'S BREATHING AS A PATIENT PRESSURE SIGNAL

2508 → DETERMINE A SMOOTHING COEFFICIENT FOR THE PATIENT PRESSURE SIGNAL

2510 → DETERMINE A DERIVATIVE SIGNAL FROM THE PATIENT PRESSURE SIGNAL

2512 → APPLY THE SMOOTHING COEFFICIENT TO THE DERIVATIVE SIGNAL

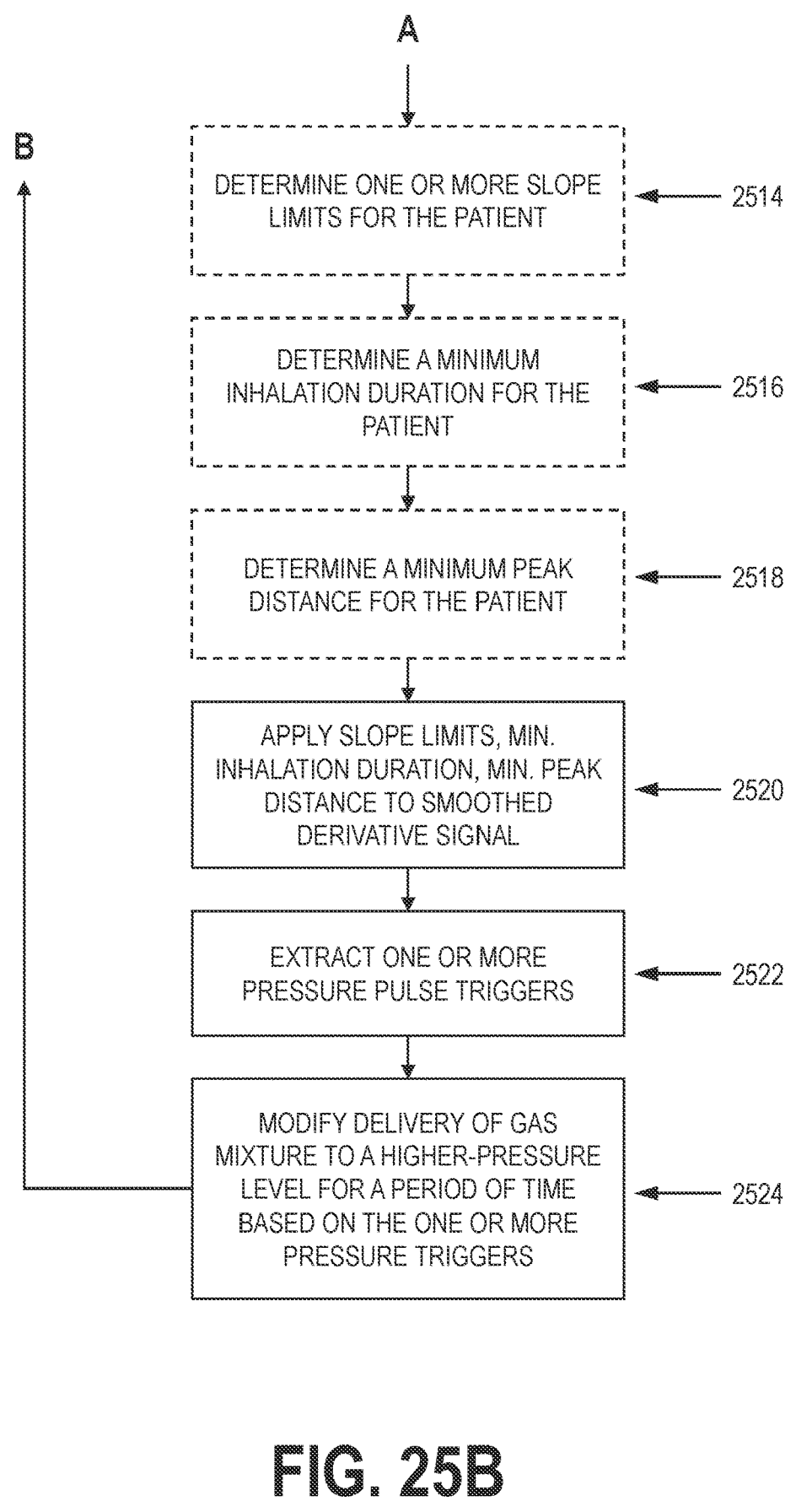

DETERMINE ONE OR MORE SLOPE LIMITS FOR THE PATIENT ◄—— 2514

DETERMINE A MINIMUM INHALATION DURATION FOR THE PATIENT ◄—— 2516

DETERMINE A MINIMUM PEAK DISTANCE FOR THE PATIENT ◄—— 2518

APPLY SLOPE LIMITS, MIN. INHALATION DURATION, MIN. PEAK DISTANCE TO SMOOTHED DERIVATIVE SIGNAL ◄—— 2520

EXTRACT ONE OR MORE PRESSURE PULSE TRIGGERS ◄—— 2522

MODIFY DELIVERY OF GAS MIXTURE TO A HIGHER-PRESSURE LEVEL FOR A PERIOD OF TIME BASED ON THE ONE OR MORE PRESSURE TRIGGERS ◄—— 2524

FIG. 25B

SYSTEMS AND METHODS FOR CONTROLLING PRESSURE SUPPORT DEVICES

CROSS-REFERENCE TO RELATED APPLICATIONS

This patent application claims the priority benefit under 35 U.S.C. § 119(e) of U.S. Provisional Application No. 63/350,438, filed on Jun. 9, 2022, the contents of which are herein incorporated by reference.

FIELD OF THE DISCLOSURE

The present disclosure is directed generally to systems and methods of controlling pressure support devices, and more specifically to systems and methods for controlling the pressure level of a gas mixture being delivered to a patient via a pressure support device.

BACKGROUND

Positive pressure support devices, such as ventilators, continuous positive airway pressure ("CPAP") machines, and the like, are a class of medical devices that support the breathing of respiratory-impaired patients. In some of these devices, like CPAP machines, a gas flow is supplied to the patient at a constant pressure level and therefore the operation of such devices does not need to be synchronized with the patient's breathing. In other devices, such as ventilator systems, the patient's breathing is supported by delivering a gas flow at a pressure level that varies with time. More specifically, the pressure support is pulsed with a higher inspiratory positive airway pressure ("IPAP") pressure level during inhalation and a lower positive end-expiratory pressure ("PEEP") pressure level during exhalation. Consequently, the action of such devices must be synchronized with the active breathing of the patient to ensure proper respiratory support. Further, the method used to determine the optimal time to trigger a pressure pulse will depend greatly upon the type and design of the ventilator system and the availability of sensor data.

SUMMARY OF THE DISCLOSURE

According to an embodiment of the present disclosure, a system for controlling a pressure level of a gas mixture being delivered to a patient is provided. The system can comprise one or more processors in communication with a ventilation system, and a memory storing instructions that, when executed by the one or more processors, cause the system to perform the following: (1) receive, from a pressure sensor of the ventilation system, a patient pressure signal; (2) generate one or more pressure triggers by: (a) determining a derivative signal based on the patient pressure signal; (b) determining a smoothed derivative signal based on the patient pressure signal and/or the derivative signal; and (c) extracting the one or more pressure triggers based on the smoothed derivative signal, wherein the one or more pressure triggers indicate an active inspiration phase of the patient's breathing; and (3) provide an instruction to the ventilation system to modify the pressure level of the gas mixture being delivered to the patient based on the one or more pressure triggers.

In an aspect, the system is configured to continuously receive the patient pressure signal over a plurality of respiratory cycles of the patient.

In an aspect, a pressure trigger is generated within 500 milliseconds for each active inspiration phase of the plurality of respiratory cycles of the patient.

In an aspect, the one or more pressure triggers are not generated during any expiration phase of the plurality of respiratory cycles of the patient.

In an aspect, the instruction provided to the ventilation system includes increasing the pressure level of the gas mixture being delivered to the patient to a higher inspiratory positive airway pressure for a period of time.

In an aspect, generating the one or more pressure triggers further includes: applying a predetermined smoothing coefficient to determine the smoothed derivative signal; and applying a predetermined slope limit and a predetermined minimum inhalation duration to the smoothed derivative signal to extract the one or more pressure triggers.

In an aspect, each of the one or more pressure triggers corresponds to a time when the smoothed derivative signal drops below the predetermined slope limit for at least the predetermined minimum inhalation duration.

According to another embodiment of the present disclosure, a ventilation system for delivering a gas mixture to a patient is provided. The ventilation system can comprise: a gas source; a gas delivery line operatively connected to the gas source; and a patient airway interface operatively connected to the gas delivery line and defining a gas flow path from the gas source to the patient, wherein the patient airway interface comprises a patient pressure sensor and one or more entrainment apertures along the gas flow path, the one or more entrainment apertures being configured to allow the patient to breath ambient air. The ventilation system can further comprise a control system having one or more processors adapted to control the delivery of the gas mixture from at least the gas source to the patient via the gas flow path, and a memory storing instructions that, when executed by the one or more processors, cause the ventilation system to perform the following: (1) deliver the gas mixture to the patient at a first pressure level via the patient airway interface and the gas flow path; (2) receive, from the patient pressure sensor, a patient pressure signal; (3) generate one or more pressure triggers by: (a) determining a derivative signal based on the patient pressure signal; (b) determining a smoothed derivative signal based on the patient pressure signal and/or the derivative signal; and (c) extracting the one or more pressure triggers based on the smoothed derivative signal, wherein the one or more pressure triggers indicate an active inspiration phase of the patient's breathing; (4) modify the pressure level of the gas mixture being delivered to the patient based on the one or more pressure triggers.

In an aspect, delivery of the gas mixture through the gas flow path and the patient airway interface generates a negative pressure area in the gas flow path at the one or more entrainment apertures.

In an aspect, the patient pressure sensor is disposed along the gas flow path in proximity with the negative pressure area generated by delivery of the gas mixture through the gas flow path and the patient airway interface.

In an aspect, the first pressure level is a positive end-expiratory pressure that is greater than zero.

In an aspect, the pressure level of the gas mixture being delivered to the patient is modified by increasing the pressure level from the first pressure level to a second pressure level, the second pressure level being a higher inspiratory positive airway pressure.

In an aspect, a combination of the gas mixture from at least the gas source and air entrained through the one or more entrainment apertures provide ventilatory support to the patient.

According to yet another embodiment of the present disclosure, a method of controlling a ventilation system attached to a patient is provided. The method can comprise: (1) delivering a gas mixture to the patient at a first pressure level via a patient airway interface and a gas flow path of the ventilation system; (2) receiving a patient pressure signal for the patient using a patient pressure sensor located along the gas flow path in proximity with a negative pressure area generated by delivery of the gas mixture; (3) generate one or more pressure triggers by: (a) determining a derivative signal based on the patient pressure signal; (b) determining a smoothed derivative signal by applying a predetermined smoothing coefficient to the patient pressure signal and/or the derivative signal; and (c) extracting one or more pressure triggers based on the smoothed derivative signals by applying a predetermined slope limit and a predetermined minimum inhalation duration to the smoothed derivative signal, wherein the one or more pressure triggers indicate an active inspiration phase of the patient's breathing; (4) providing an instruction to the ventilation system to modify the pressure level of the gas mixture being delivered to the patient based on the one or more pressure triggers; and (5) modifying the pressure level of the gas mixture being delivered to the patient for a period of time based on the provided instruction, wherein the pressure level is modified by increasing the pressure level of the gas mixture being delivered to the patient to a higher inspiratory positive airway pressure for the period of time.

In an aspect, the patient pressure signal is received continuously from the patient pressure signal over a plurality of respiratory cycles of the patient, the one or more pressure triggers are generated for each active inspiration phase of the plurality of respiratory cycles of the patient, and the gas mixture is delivered to the patient at the higher inspiratory positive airway pressure for the period of time within 500 milliseconds of each active inspiration phase of the plurality of respiratory cycles of the patient.

These and other aspects of the various embodiments will be apparent from and elucidated with reference to the embodiments described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIGS. 25A and 25B are flowcharts illustrating a method of controlling the pressure level of a ventilation system according to aspects of the present disclosure.

DETAILED DESCRIPTION OF EMBODIMENTS

The present disclosure relates to systems and methods of controlling pressure support devices. More specifically, the present disclosure relates to systems and methods for controlling the pressure level of a gas mixture being delivered to a patient via a pressure support device adapted to provide breathing support to a patient that varies with time. As described herein, the systems and methods enable pressure pulse control that is triggered only during the active inspiration phases of the patient's respiratory cycles (i.e., never during an expiration phase), where every inspiration phase meeting certain criteria is supported by a pressure pulse, and where the trigger delay (i.e., the time between detecting an active inspiration phase and the triggering of the pressure pulse) is no greater than about 500 milliseconds. Additionally, the systems and methods described herein are adapted to function based solely on the measured patient pressure as discussed below, but it is contemplated that other techniques, methods, and devices may be used in conjunction with the measured patient pressure.

Figure 1:
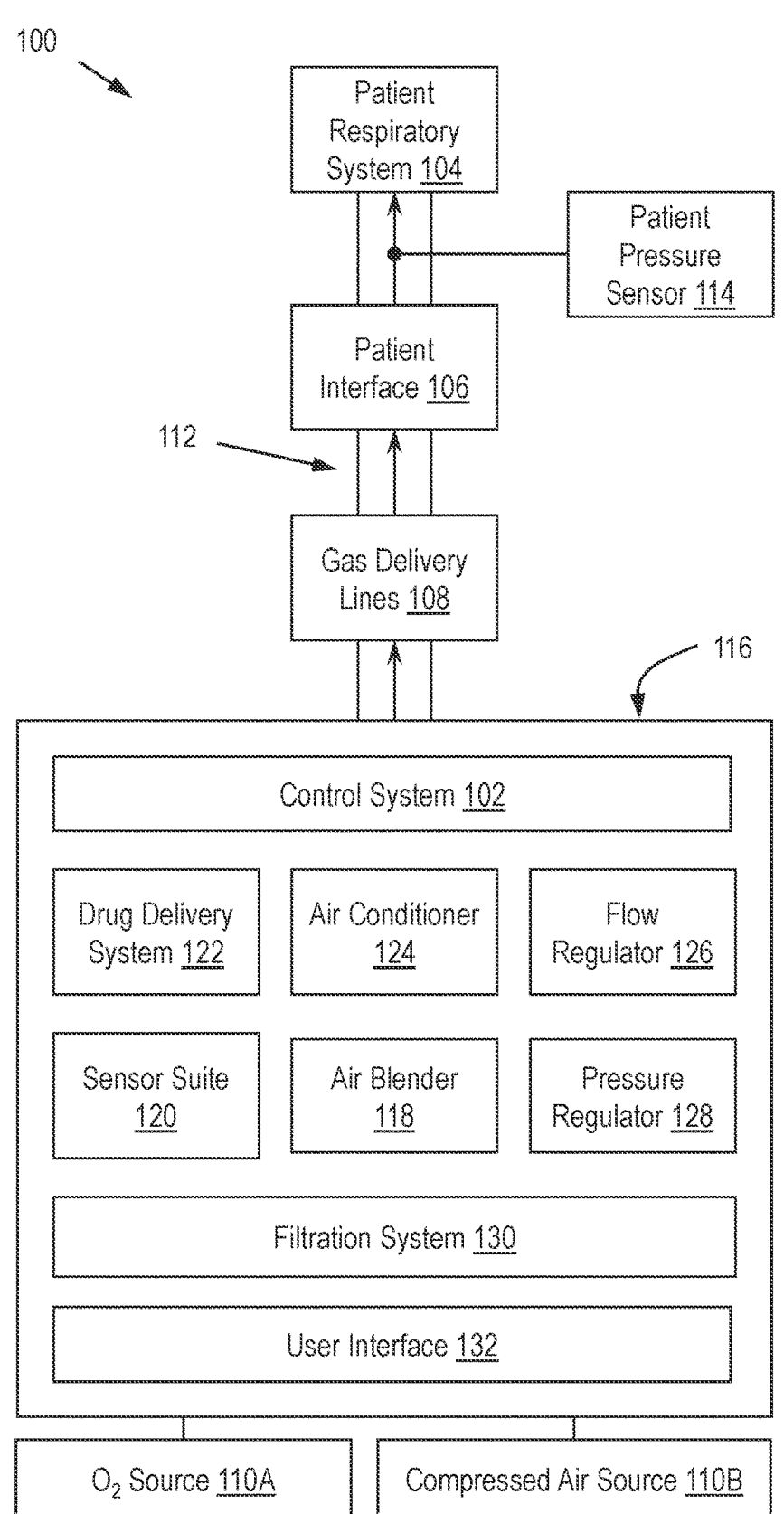
FIG. 1 is a block diagram illustrating a ventilation system according to aspects of the present disclosure.

Turning to FIG. 1, a block diagram of a ventilation system 100 having an integrated pressure control sub-system 102 is illustrated according to aspects of the present disclosure. When using the ventilation system 100, the ventilation system 100 is attached to the respiratory system 104 of a patient through which the patient breathes normally while receiving mechanical support via a patient airway interface 106. In embodiments, the patient airway interface 106 may be a non-invasive interface, such as a non-invasive open nasal interface. In addition to the patient airway interface 106, the ventilation system 100 can include a gas delivery line 108 operatively connected to a gas source 110 (e.g., an oxygen source 110A and/or a compressed air source 110B). At least the gas delivery line(s) 108 and the patient airway interface 106 will define a gas flow path 112 from the gas source(s) 110A, 110B to the patient's respiratory system 104.

In embodiments, the ventilation system 100 further includes a patient pressure sensor 114 disposed along the gas flow path 112 and adapted to measure the pressure generated by each of the patient's respiratory cycles (e.g., cycles of inhaling and exhaling). In particular embodiments, the patient pressure sensor 114 may be disposed within the patient airway interface 106.

Figure 2:
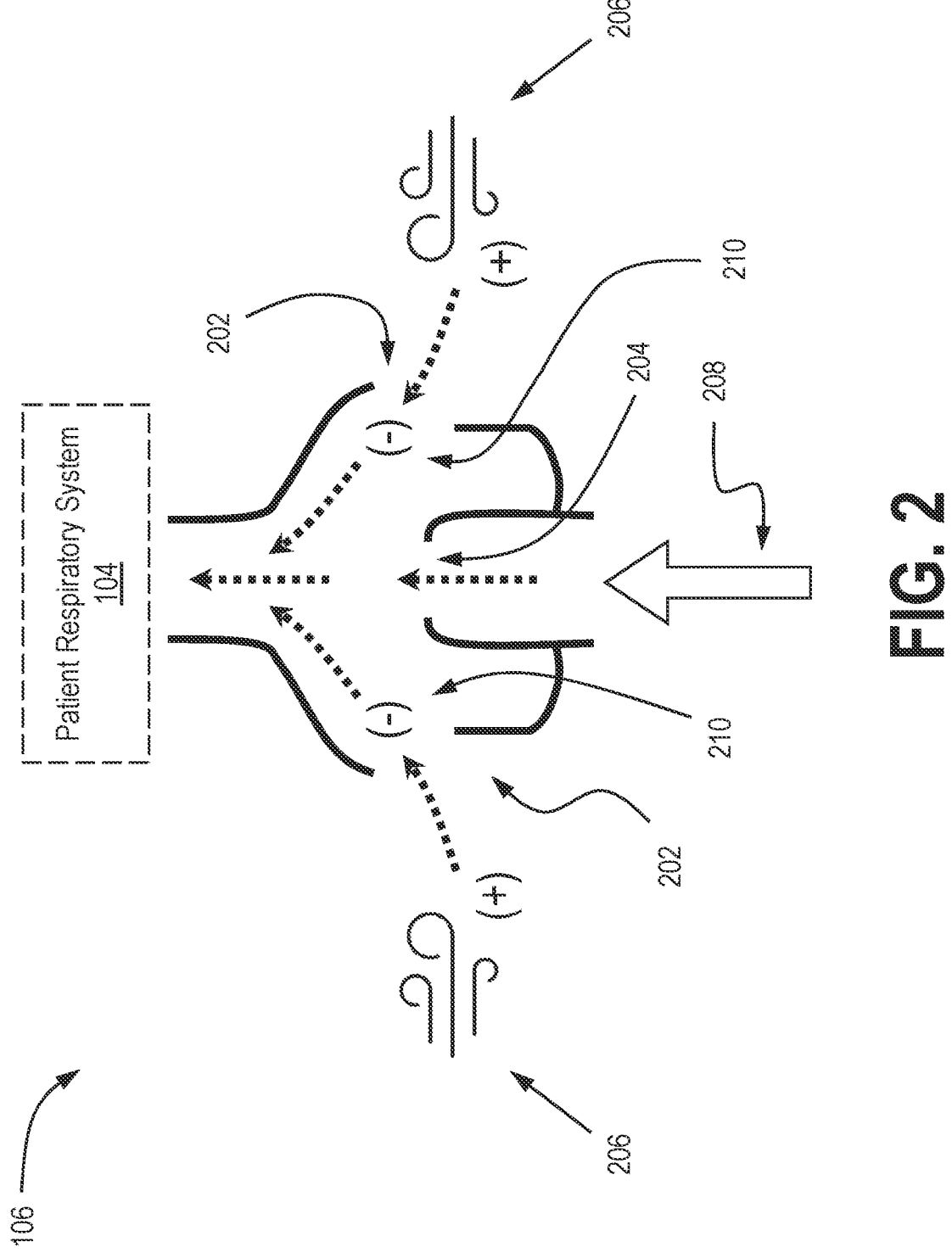
FIG. 2 is a diagram illustrating the gas flow through a portion of a patient airway interface according to aspects of the present disclosure.

With reference to FIG. 2, the patient airway interface 106 may further include one or more entrainment apertures 202. As seen in FIG. 2, a primary flow 208 of a gas mixture can be delivered to the patient's respiratory system 104 through a narrow opening 204 of the patient airway interface 106. During normal operation, the ventilation system 100 can provide ventilatory support in the form of the primary gas flow 208 (e.g., a gas mixture) delivered to the patient 104 that varies with time. That is, the pressure level and flow rate of the primary gas flow 208 can be varied over time via the ventilation system 100.

In an aspect, the primary flow 208 is delivered at a first pressure level (i.e., a baseline pressure level) that is greater than zero. For example, during the exhalation phases of the patient's respiratory cycle, the gas flow 208 may be delivered at a positive end-expiratory pressure ("PEEP") pressure level. In specific embodiments, the first pressure level is greater than zero cmH₂O, including from about 1 cmH₂O to about 10 cmH₂O, from about $_2$ cmH₂O to about 9 cmH₂O, from about 3 cmH₂O to about 8 cmH₂O, from about 4 cmH₂O to about 7 cmH₂O, from about 5 cmH₂O to about 6 cmH₂O, and any combination of endpoints thereof.

Because the primary flow 208 may be forced through a narrow opening 204 according to the present disclosure, an entrainment of surrounding air 206 is produced within a portion of the patient airway interface 106. That is, the primary gas flow 112 is forced along the gas flow path 112, which includes a narrow opening 204 that generates a negative pressure area(s) 210 in the gas flow path 112 at the one or more entrainment apertures 202. Although an efficient retainment of surrounding air is produced, the velocity of the primary flow 208 within the patient airway interface 106 will be very high (i.e., close to the velocity of sound), which will create significant fluctuations and step changes in the flow pattern within this region of the patient airway interface 106. As a result, the total gas flow to the patient cannot be measured within the patient airway interface 106 of such ventilation systems 100 and the measured patient pressure (i.e., the pressure produced by the patient's breathing) will contain significant amounts of artifacts and noise.

Figure 3:
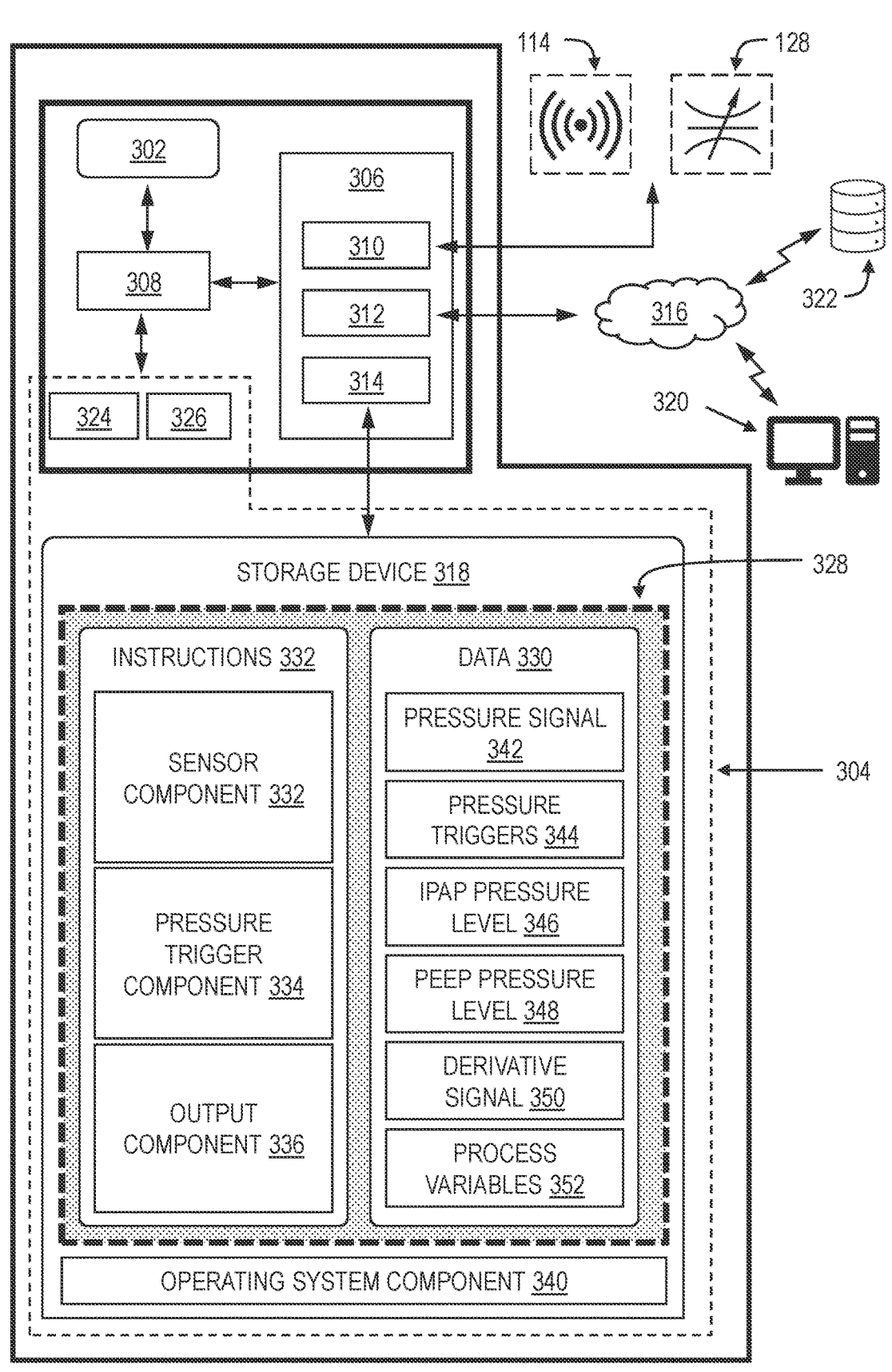
FIG. 3 is a schematic diagram illustrating a system used for controlling the pressure level of an associated pressure support device according to aspects of the present disclosure.

According to certain aspects of the present disclosure, a system 300 for controlling the pressure level of a gas mixture 112 being delivered to a patient 104 is described. With reference to FIG. 3, one such system 300 is schematically illustrated. The pressure controlling system 300 can comprise one or more processors 302 (also referred to as central processing units or CPUs), machine-readable memory 304, and an interface bus 306, all of which may be interconnected and/or communicate through a system bus 308 containing conductive circuit pathways through which instructions (e.g., machine-readable signals) may travel to effectuate communications, tasks, storage, and the like.

In embodiments, the one or more processors 302 can comprise a high-speed data processor adequate to execute program components, which may include various specialized processing units as may be known in the art. The general processor may be a microprocessor, or may also be any traditional processor, controller, microcontroller, or state machine. In some embodiments, one or more of the features described herein may be implemented on components such as an Application-Specific Integrated Circuit ("ASIC"), a Digital Signal Processor ("DSP"), a Field Programmable Gate Array ("FPGA"), or similar electronics.

In embodiments, the interface bus 306 may include an input/output interface 310 configured to connect the system 300 to one or more peripheral devices (e.g., the patient pressure sensor 114, the pressure regulator 128, the ventilator module 116, etc.), a network interface 312 configured to connect the pressure controlling system 300 to a communications network 316 (e.g., using a network protocols such as IEEE 802.3 and/or 802.11), and/or a storage interface 314 configured to accept, communicate, and/or connect to a number of machine-readable memory devices (e.g., storage device 318, removable storage devices, etc.).

In aspects, the network interface 312 operatively connects the pressure controlling system 300 to a communications network 316, which can include a direct interconnection, the Internet, a local area network ("LAN"), a metropolitan area network ("MAN"), a wide area network ("WAN"), a wired or Ethernet connection, a wireless connection, and similar types of communications networks, including combinations thereof. In some embodiments, one or more user devices 320 and/or databases 322 may connect with the pressure controlling system 300 via the communications network 316 and the network interface 312.

In embodiments, the memory 304 can be variously embodied in one or more forms of machine-accessible and machine-readable memory, including a various types of storage devices 318, random access memory 324, and read-only memory 326. In aspects, the storage device 318 can include a non-transitory storage medium, a magnetic disk storage, an optical disk storage, an array of storage devices, a solid-state memory device, and the like, including combinations thereof.

Figure 4:
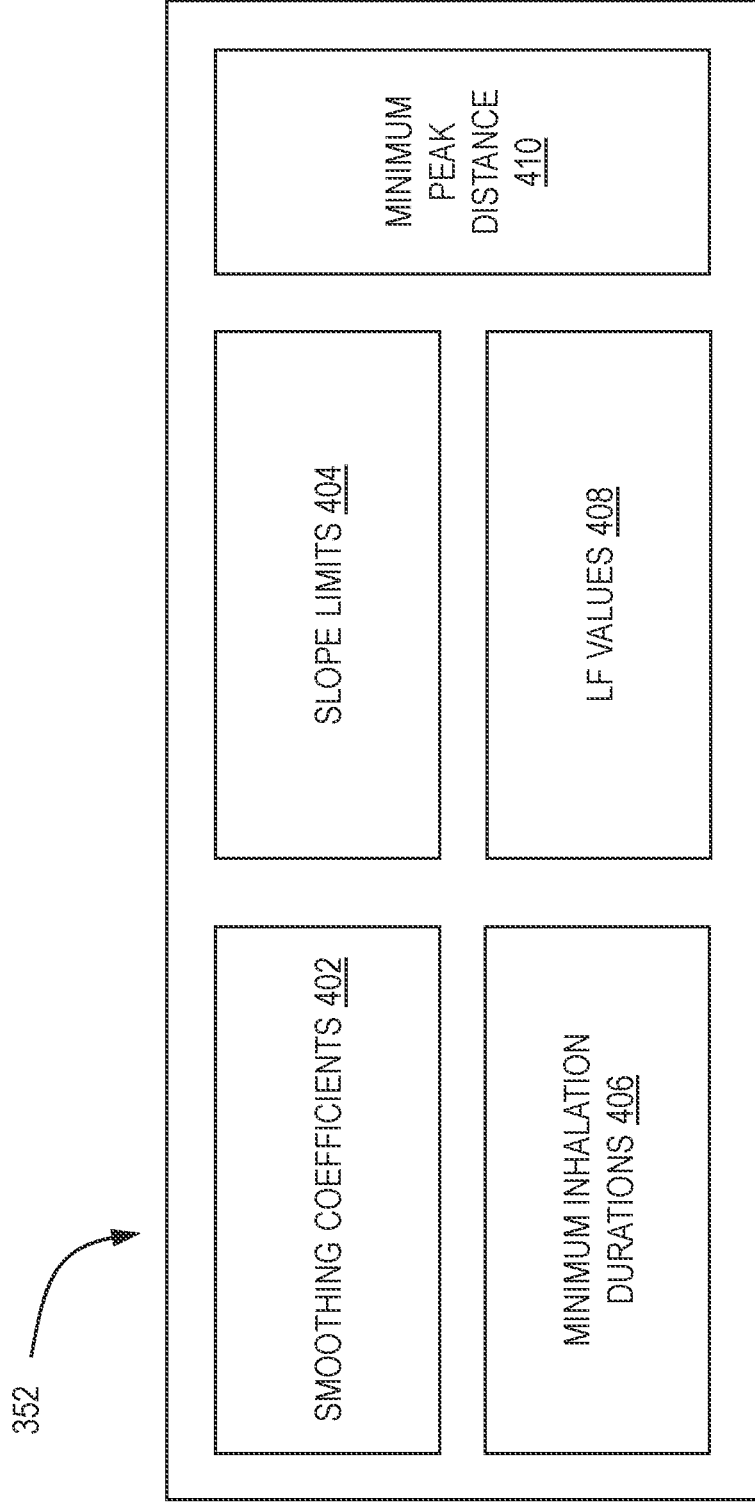
FIG. 4 is a block diagram illustrating particular types of process variables according to aspects of the present disclosure.

In embodiments, memory 304 can include a pressure trigger module 328 that includes a collection of programs and/or database components and/or data (e.g., data 330). In an aspect, for example, the data 330 can include one or more process variables 352, including but not limited to, smoothing coefficients, slope limits, inhalation durations, and the like (as discussed below and shown in FIG. 4). Depending on the particular implementation, the pressure trigger module 328 may include software components, hardware components, and/or some combination of both hardware and software components.

In particular embodiments, the pressure trigger module 328 can include, but it not limited to, instructions 332 having a sensor component 334, a pressure trigger component 336, and an output component 336. These components may be incorporated into, loaded from, loaded onto, or otherwise operatively available to and from the pressure controlling system 300. Similarly, the pressure controlling system 300 can be incorporated into, loaded from, loaded onto, or otherwise operatively available to and from the ventilation system 100. For example, although program components may be stored in a local storage device 318, they may also be loaded and/or stored in other memory, such as a remote cloud storage facility accessible through a communications network (e.g., communications network 316).

The memory 304 of the pressure controlling system 300 can also include an operating system component 340. The operating system component 340 can be an executable program component facilitating the operation of the pressure controlling system 300. Typically, the operation system component 340 is configured to facilitate access of the I/O, network, and storage interfaces, and may communicate with other components of the pressure controlling system 300.

In embodiments, the sensor component 332 can be a stored program component that is executed by at least one processor, such as the one or more processors 302 of the pressure controlling system 300. In particular, the sensor component 332 can be configured to measure and/or receive a patient pressure signal 342 from a pressure sensor 114 of a ventilation system 100. In embodiments, patient pressure signal 342 may include a plurality of respiratory cycles of the patient. That is, the patient pressure signal 342 may be continuously received and/or received in real-time. In an aspect, each respiratory cycle of the patient can include one inhalation phase and one exhalation phase, and therefore the patient pressure signal 342 can include one or more inhalation phases and one or more exhalation phases. The sensor component 332 may then provide the received patient pressure signal 342 to the pressure trigger component 334.

In embodiments, the pressure trigger component 334 can be a stored program component that is executed by at least one processor, such as the one or more processors 302 of the pressure controlling system 300. In particular, the pressure trigger component 334 can be configured to generate one or more pressure triggers 344. Each pressure trigger 344 indicates an active inspiration phase of the patient's breathing (i.e., respiratory cycle), and thus, indicates when the gas flow 208 should be delivered to the patient 104 at a higher inspiratory positive airway pressure ("IPAP") pressure level 346.

In embodiments, the pressure trigger component 334 can be configured to: (i) determine a derivative signal 350 based on the patient pressure signal 342; (ii) determine a smoothed derivative signal 350 based on the patient pressure signal 342 and/or the derivative signal 350 using one or more smoothing coefficients 402; and (iii) extract the one or more pressure triggers 344 based on the smoothed derivative signal 350. In an aspect, the smoothed derivative signal 350 may be determined and smoothed in one step. For example, the following operation may be performed using the patient pressure signal 342:

$$\frac{dPy_i}{dt} = \frac{1}{\Delta t} \cdot \sum_{k=-Lf}^{Lf} Co_k \cdot Py_{i+k}$$

$$\text{with } Co_k = \frac{k}{\sum_{m=-Lf}^{Lf} m^2}$$

where dPy/dt is the smoothed derivative signal 350, $\Delta t$ is a time step, Lf ("LF value" 408 shown in FIG. 4) is an integer greater than zero that corresponds to a number of data points to be smoothed over, $Co_k$ is a smoothing coefficient 352, Py is the patient pressure signal 342, and k, i, and m are integers greater than zero.

In some embodiments, the Lf value 408 can be from about 2 to about 50, including from about 5 to about 40, from about 10 to about 30, from about 15 to about 20, from about 8 to about 32, and any combination of endpoints thereof. However, the Lf value 408 is preferably minimized to avoid excessive trigger delays.

In embodiments, the pressure trigger component 334 can be further configured to: (iv) apply one or more predetermined slope limits 404 to the smooth derivative signal 350; (v) apply one or more predetermined minimum inhalation durations 406 to the smoothed derivative signal 350; (vii) apply one or more predetermined minimum peak distances 410 to the smoothed derivative signal 350; (viii) determine one or more slope limits 404 to be applied to the smooth derivative signal 350; (ix) determine one or more minimum inhalation durations 406; (xi) determine one or more minimum peak distances 410; and/or (x) determine one or more Lf values 408. In an aspect, one or more of the process variables 352 may be predetermined or preset by a physician or therapy provider, or may be adjusted by the pressure controlling system 300 and/or patient to meet the physiological needs of the patient.

In an aspect, the slope limits 404 can be from about ±2 cmH₂O/s to about ±20 cmH₂O/s, including from about ±3 cmH₂O/s to about ±15 cmH₂O/s, from about ±5 cmH₂O/s to about ±10 cmH₂O/s, from about ±7 cmH₂O/s to about ±9 cmH₂O/s, and any combination of points thereof In an aspect, one or both of the first and second pressure levels 348, 346 (i.e., the lower PEEP pressure level 348 and the higher IPAP pressure level 346) may be predefined by a physician or therapy provider, or may be adjusted by the patient themself. In specific embodiments, the first pressure level 348 can be from about 0.0 cmH₂O to about 30 cmH₂O, including from about 0.0 cmH₂O to about 10 cmH₂O. In an aspect, the first pressure level 348 is greater than 0.0 cmH₂O and less than 30 cmH₂O, or is greater than 0.0 cmH₂O and less than about 10 cmH₂O. In further embodiments, the second pressure level 346 can be from about 2 cmH₂O to about 30 cmH₂O, including from about 2 cmH₂O to about 20 cmH₂O, and from about 10 cmH₂O to about 20 cmH₂O. In an aspect, the second pressure level 346 is greater than the first pressure level 348.

Turning to FIG. 5 through FIG. 17, the disclosed systems and methods are now described and illustrated in connection with simulated data for an adult with chronic obstructive pulmonary disorder ("COPD") with 20 breaths per minute and active expiration with a constant primary flow yielding a PEEP pressure level 348 of about 5.3 cmH₂O. The sampling rate of the simulated data is Δt=2 ms.

Figure 5:
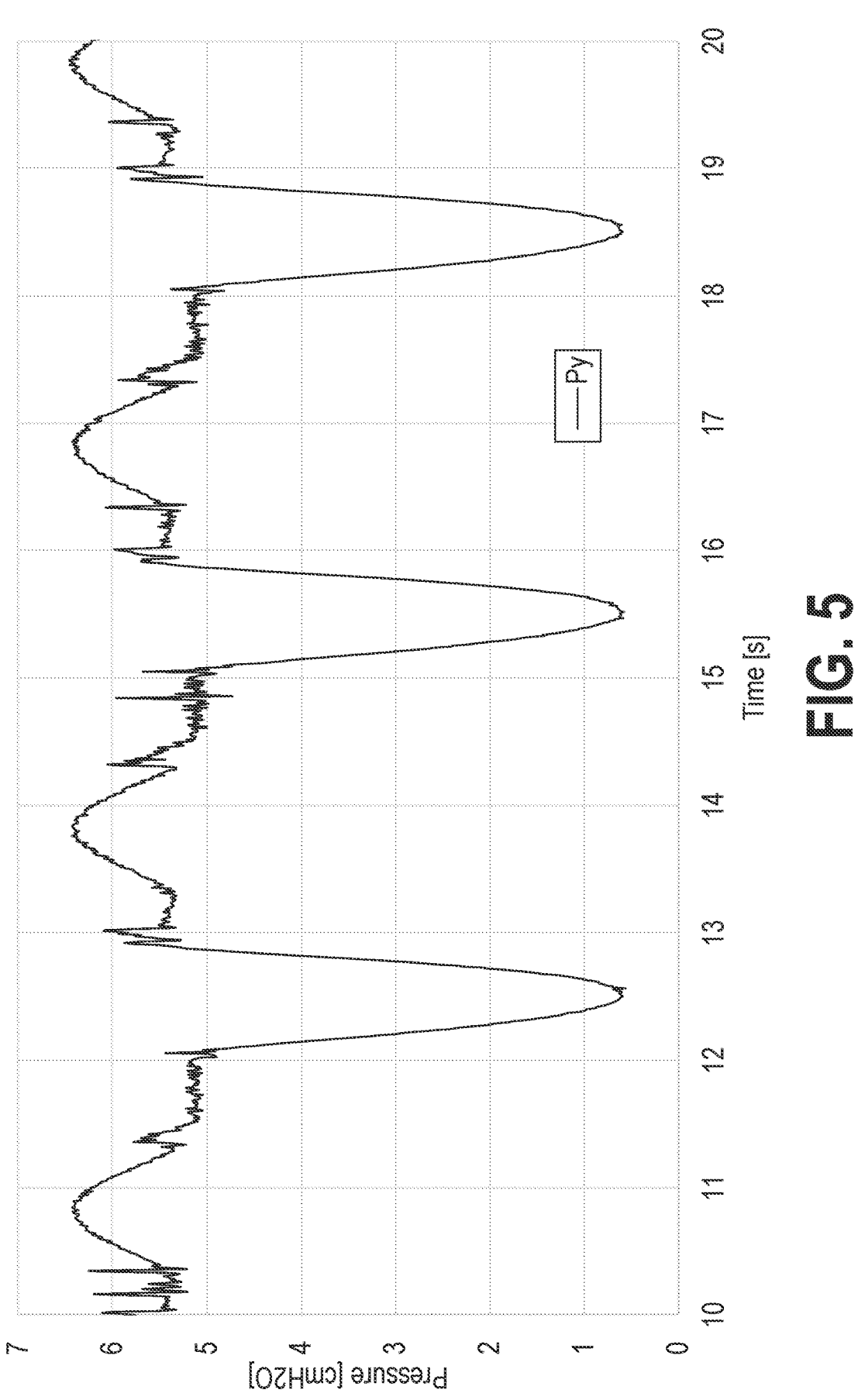
FIG. 5 is a graph illustrating a first simulated patient pressure signal over a period of time according to aspects of the present disclosure.

As shown in FIG. 5, a patient pressure signal (Py) 342 for a plurality of respiratory cycles is illustrated between t=10 seconds and t=20 seconds. The broad dips or valleys correspond to the patient's inhalation phases, while the broad hills correspond to the patient's exhalation phases. As discussed above, however, the patient pressure signal 342 contains a significant amount of noise, as seen by the sharp peaks and step changes, which can be caused by flow pattern fluctuations within the patient airway interface 106.

Figure 6:
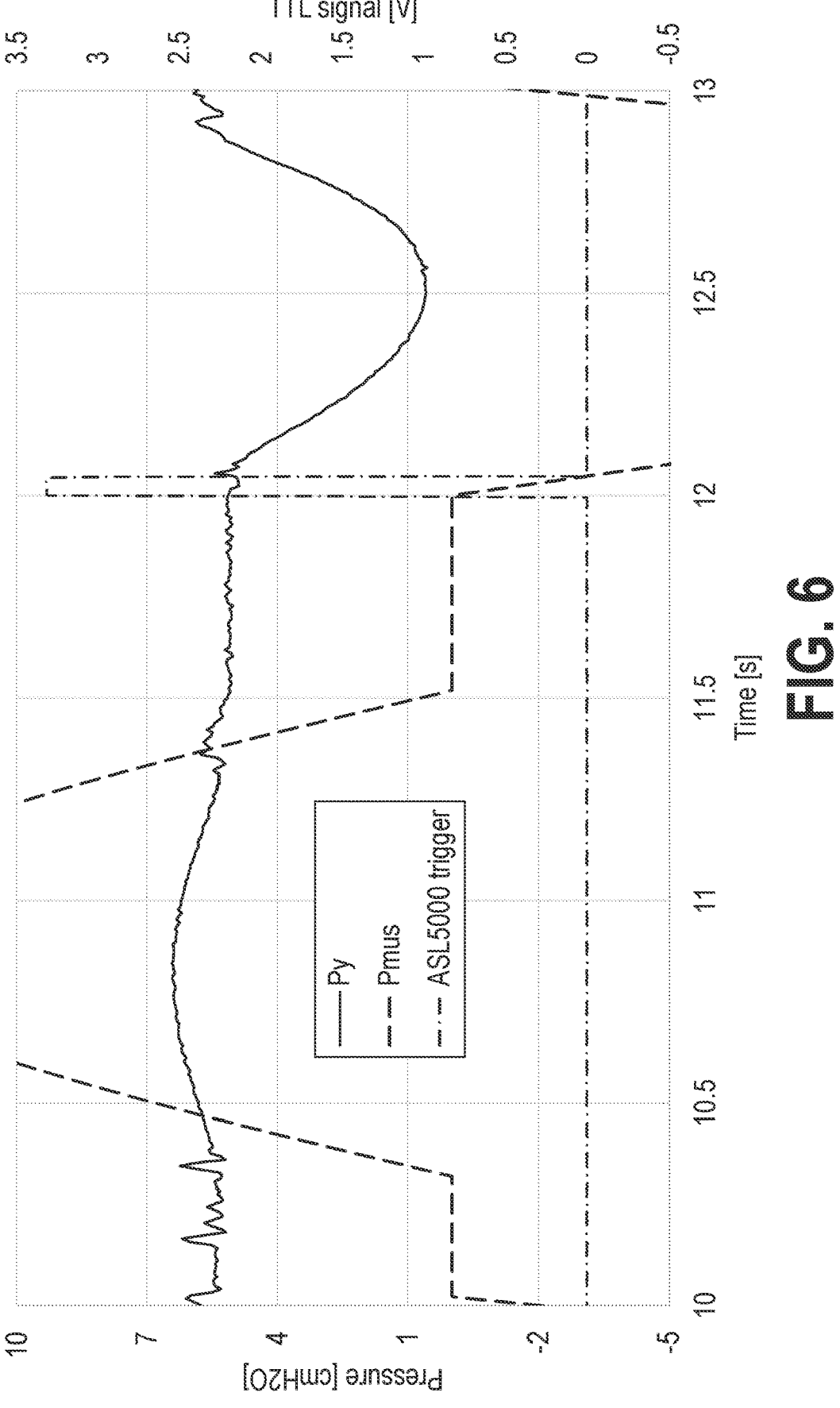
FIG. 6 is a graph illustrating a patient pressure signal, a patient muscle activation signal, and an example trigger signal according to aspects of the present disclosure.
Figure 7:
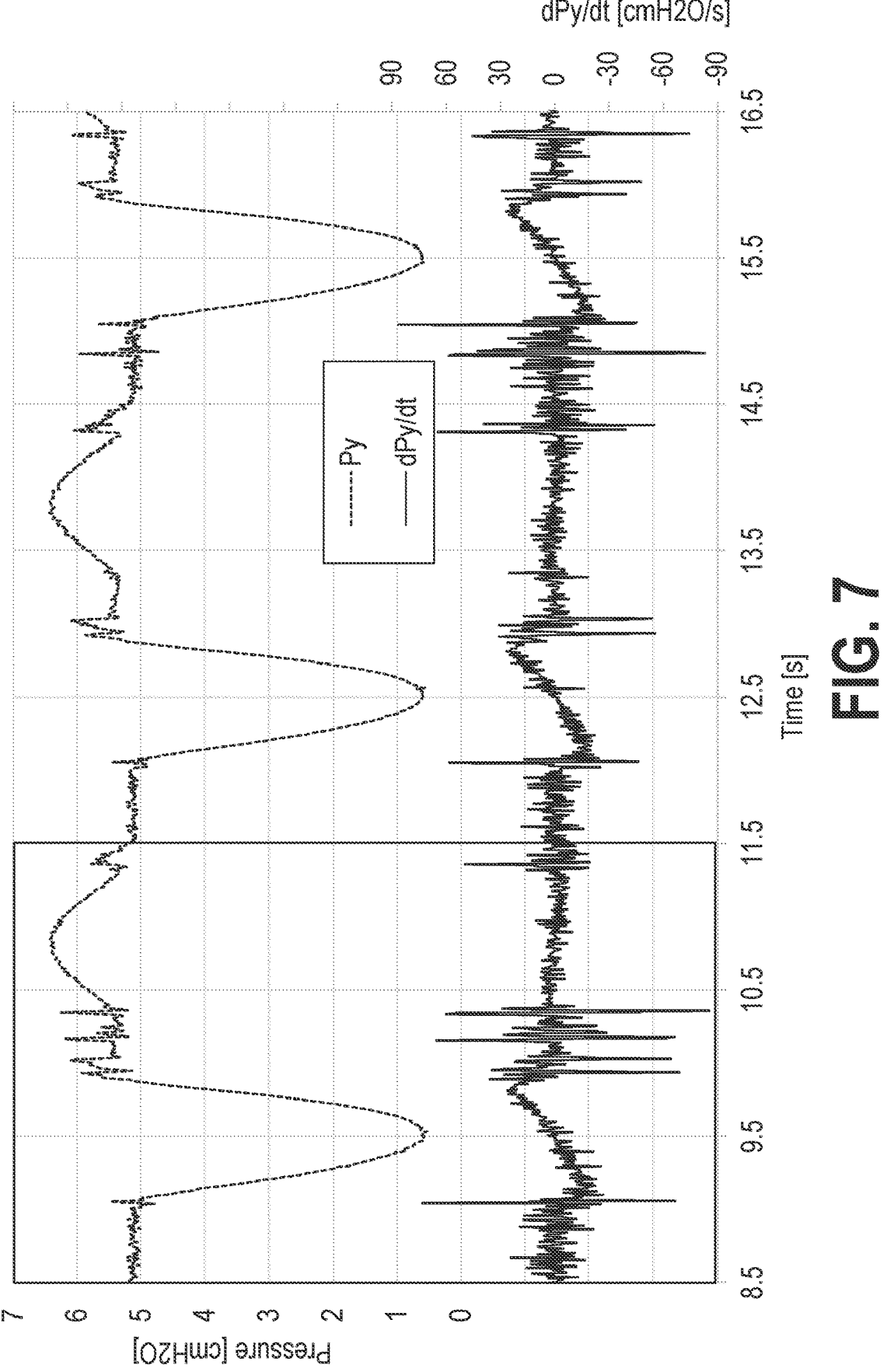
FIG. 7 is a graph illustrating a patient pressure signal and an unsmoothed derivative signal according to aspects of the present disclosure.

In certain conventional pressure support devices, the patient's muscular pressure signal can be utilized to determine when to trigger respiratory support. For example, as shown in FIG. 6, the patient pressure signal (Py) 342 is shown for approximately one respiratory cycle between t=10 seconds and t=13 seconds, a simulated patient muscular pressure signal (Pmus), and a trigger output signal (ASL 5000 trigger) at the start of Pmus action. While the patient's muscular pressure signal (Pmus) can be used to easily trigger pressure support in conventional pressure support devices, it is not trivial to rely primarily on the noisy patient pressure signal (Py) 342 shown in FIG. 5.

Figure 8:
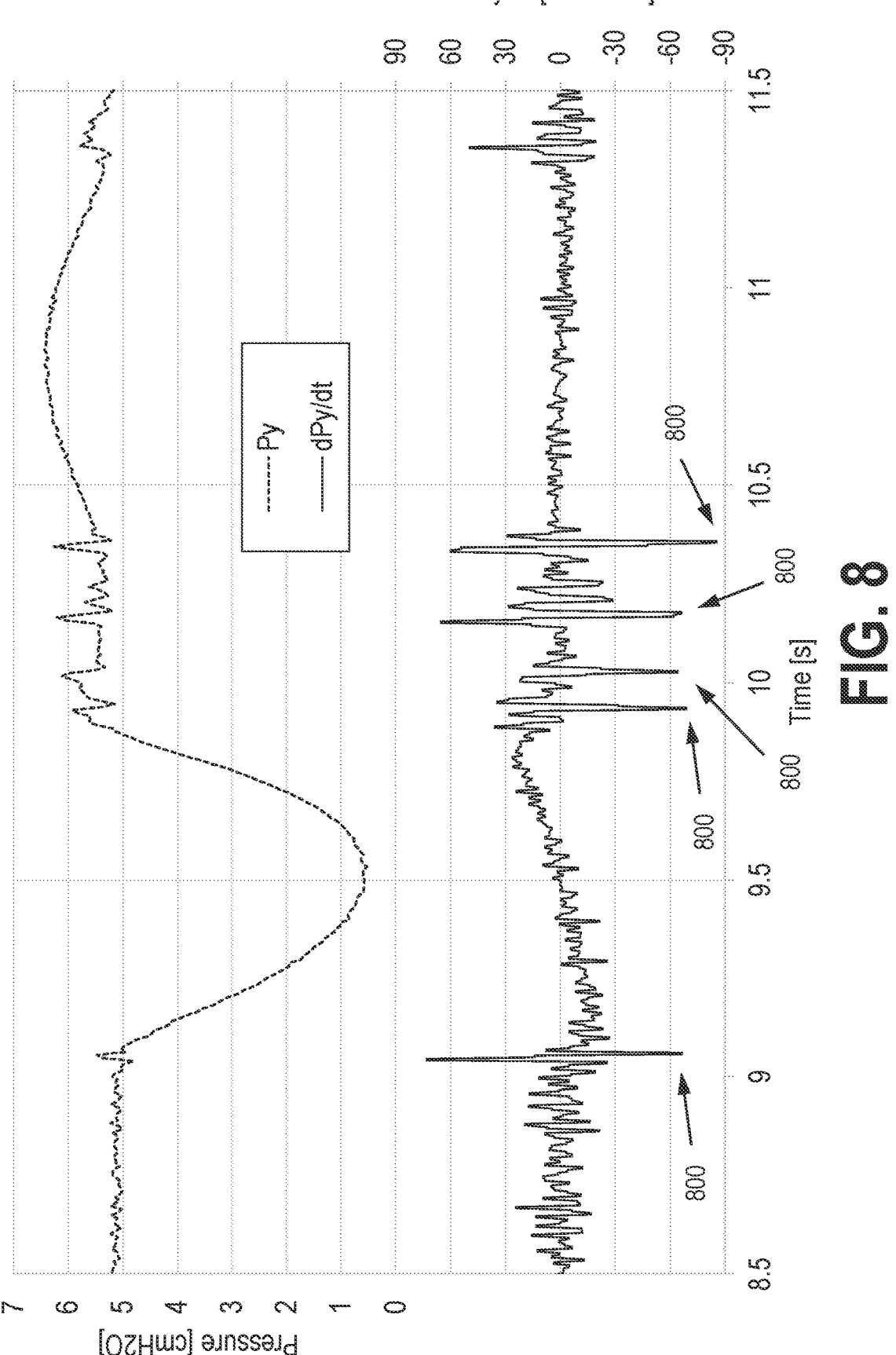
FIG. 8 is a graph showing the portion of FIG. 7 from t=8.5 seconds to t=11.5 seconds.
Figure 9:
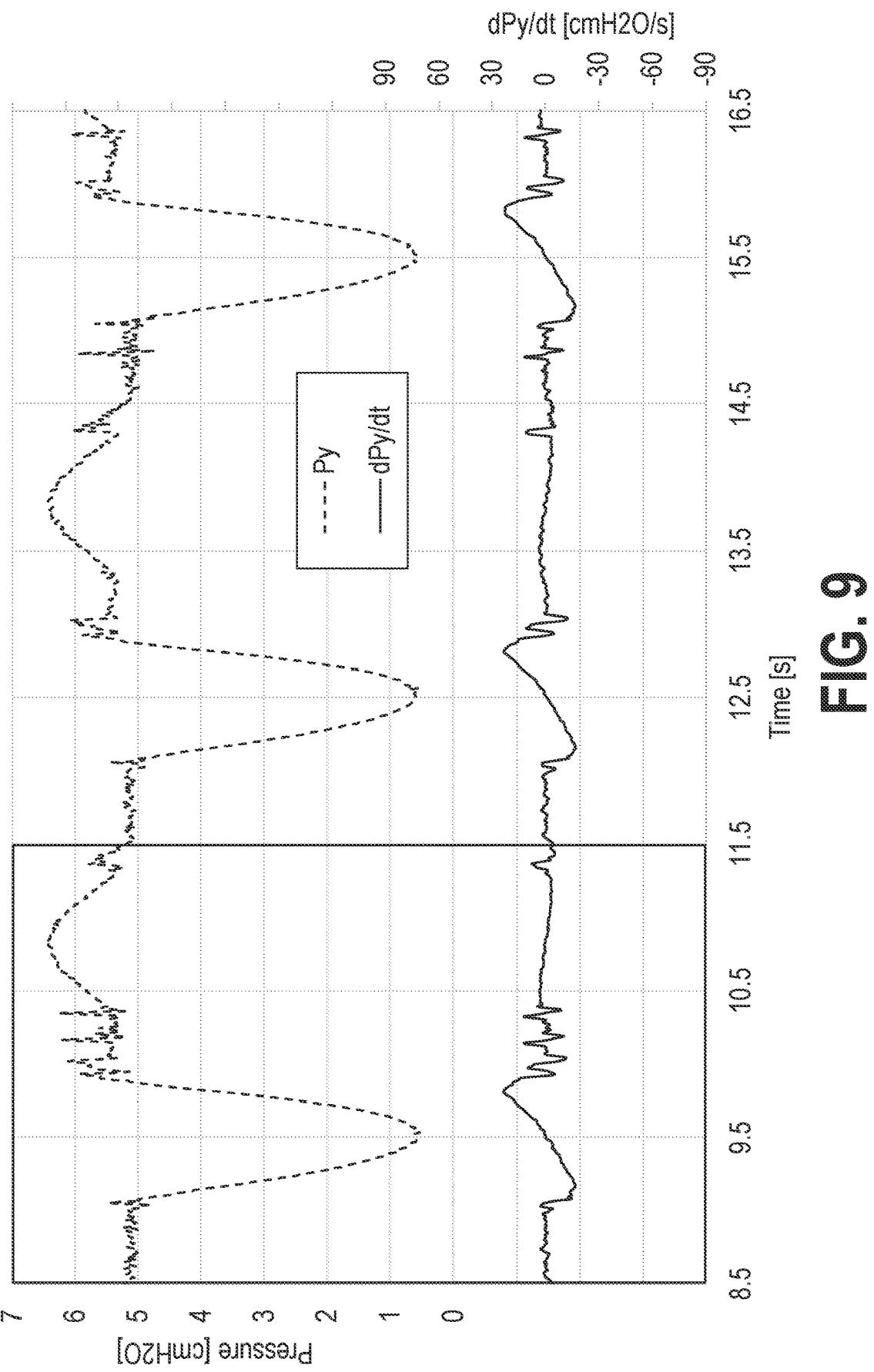
FIG. 9 is a graph illustrating a patient pressure signal and a smoothed derivative signal according to aspects of the present disclosure.
Figure 10:
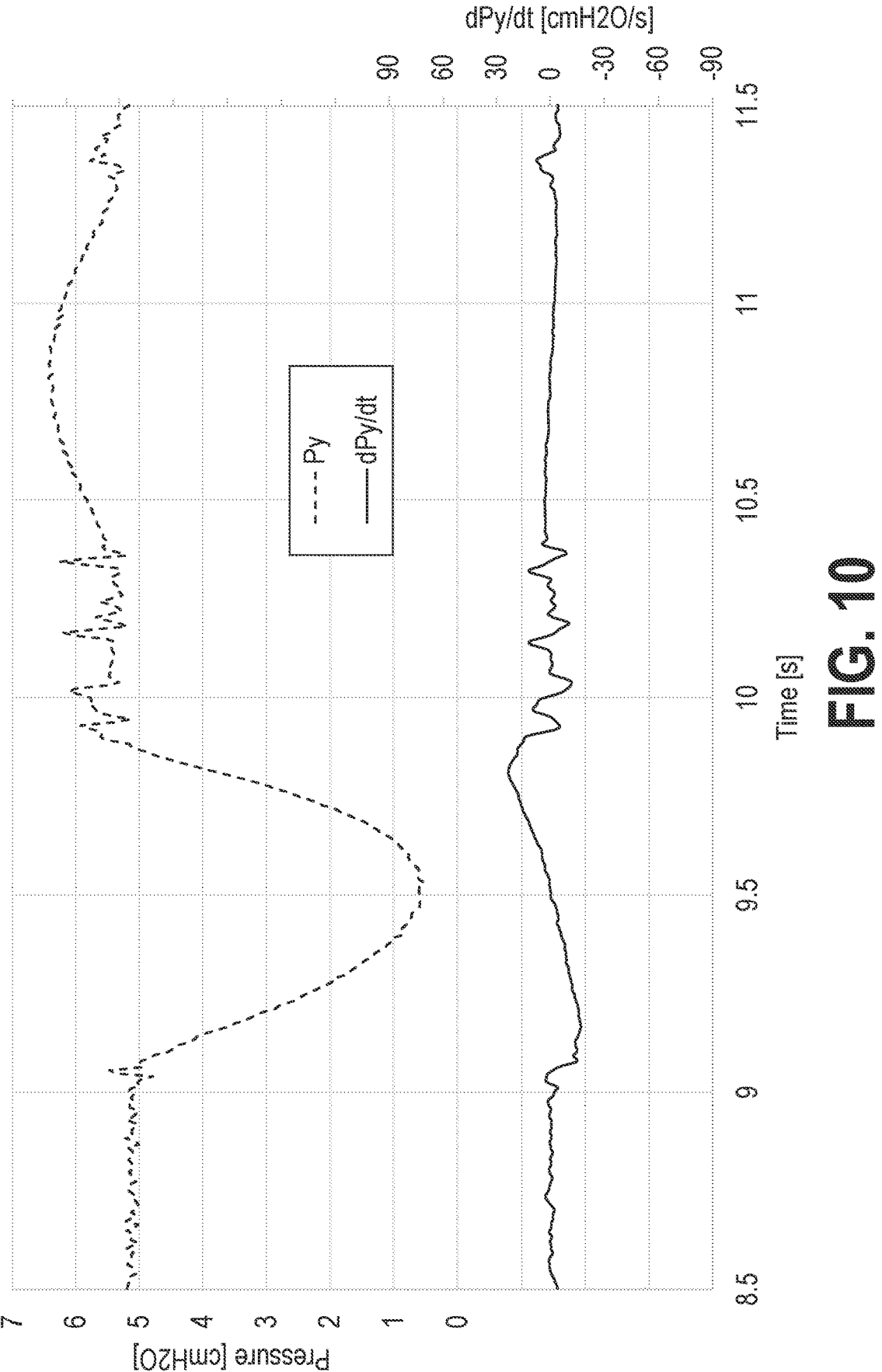
FIG. 10 is a graph showing the portion of FIG. 9 from t=8.5 seconds to t=11.5 seconds.

According to the present disclosure, the pressure controlling system 300 can generate and/or determine a derivative signal (dPy/dt) 350 based on the patient pressure signal (Py) 342 as discussed herein. For example, the derivative signal (dPy/dt) 350 shown in FIGS. 7 and 8 were determined using an Lf value of 1 (i.e., no smoothing). However, as noted above, the derivative signal (dPy/dt) 350 remains significantly noisy. In particular, FIG. 8 illustrates a section of FIG. 7, from t=8.5 seconds to t=11.5 seconds, which shows the derivative signal (dPy/dt) 350 having multiple "valleys" 800 that might indicate the start of an active inspiration phase even when the patient pressure signal (Py) 342 does not support such a conclusion.

Thus, as described herein, the pressure controlling system 300 may be configured to apply a smoothing process to the patient pressure signal (Py) 342 and/or the derivative signal (dPy/dt) 350 to obtain a smoothed derivative signal (dPy/dt) 350. For example, the derivative signal (dPy/dt) 350 shown in FIGS. 9 and 10 were obtained using an Lf of 16. When comparing the derivative signal (dPy/dt) 350 shown in FIG. 8 and the derivative signal (dPy/dt) 350 shown in FIG. 10, the derivative signal (dPy/dt) 350 shown in FIG. 10 clearly contains less "noise."

Figure 11:
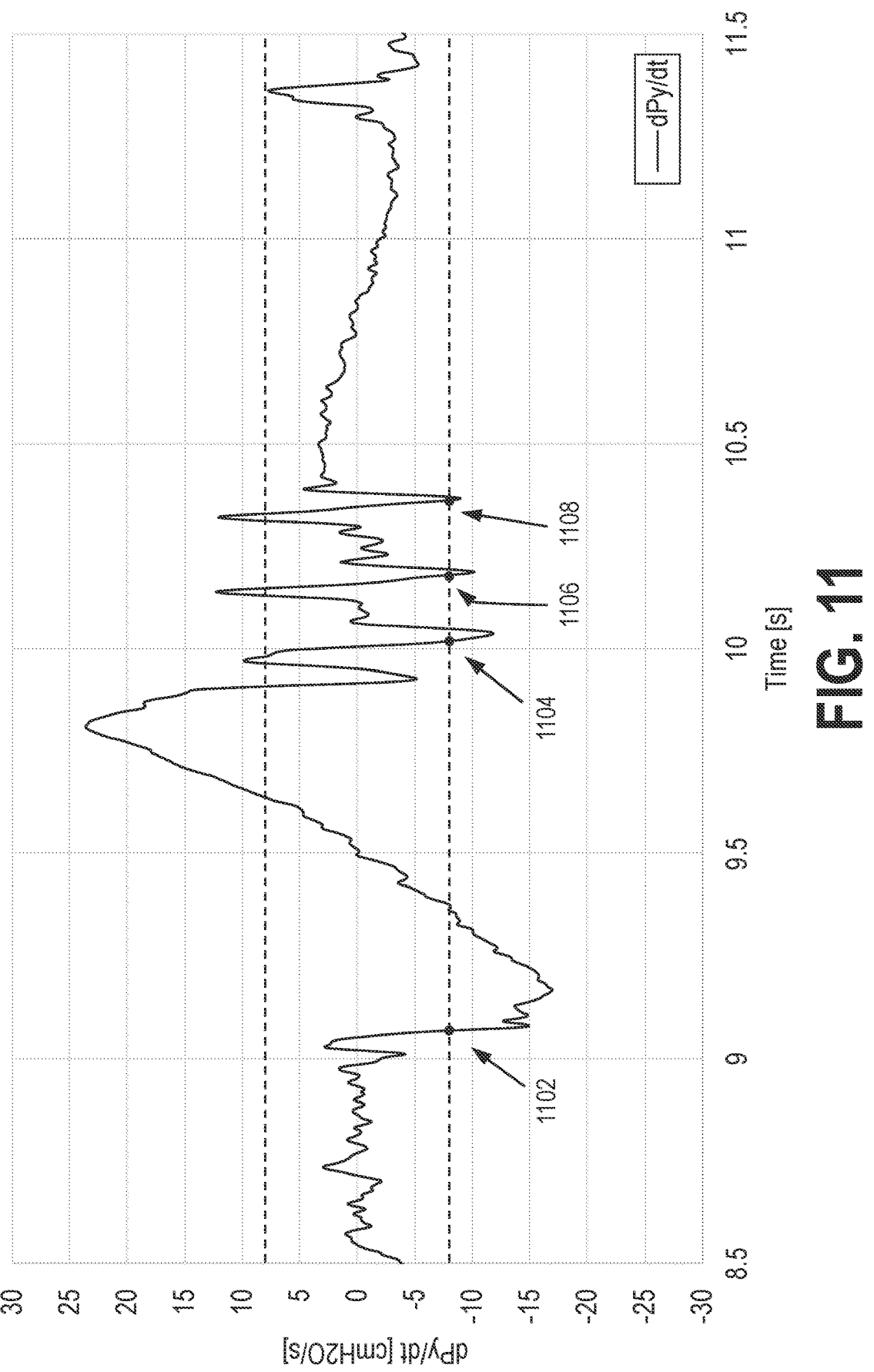
FIG. 11 is a graph illustrating the smoothed derivative signal from FIG. 10 with one or more slope limits according to aspects of the present disclosure.

Using this smoothed derivative signal (dPy/dt) 350, the pressure controlling system 300 can then apply one or more predetermined slope limits 404 to determine one or more pressure triggers 344 corresponding to the start of an active inspiration phase of the patient's respiratory cycle. With reference to FIG. 11, slope limits 404 of ±8 cmH₂O/s are applied to the smoothed derivative signal (dPy/dt) 350 to identify several points 1102, 1104, 1106, 1108 where the smoothed derivative signal (dPy/dt) 350 drops below the lower slope limit 404.

Figure 12:
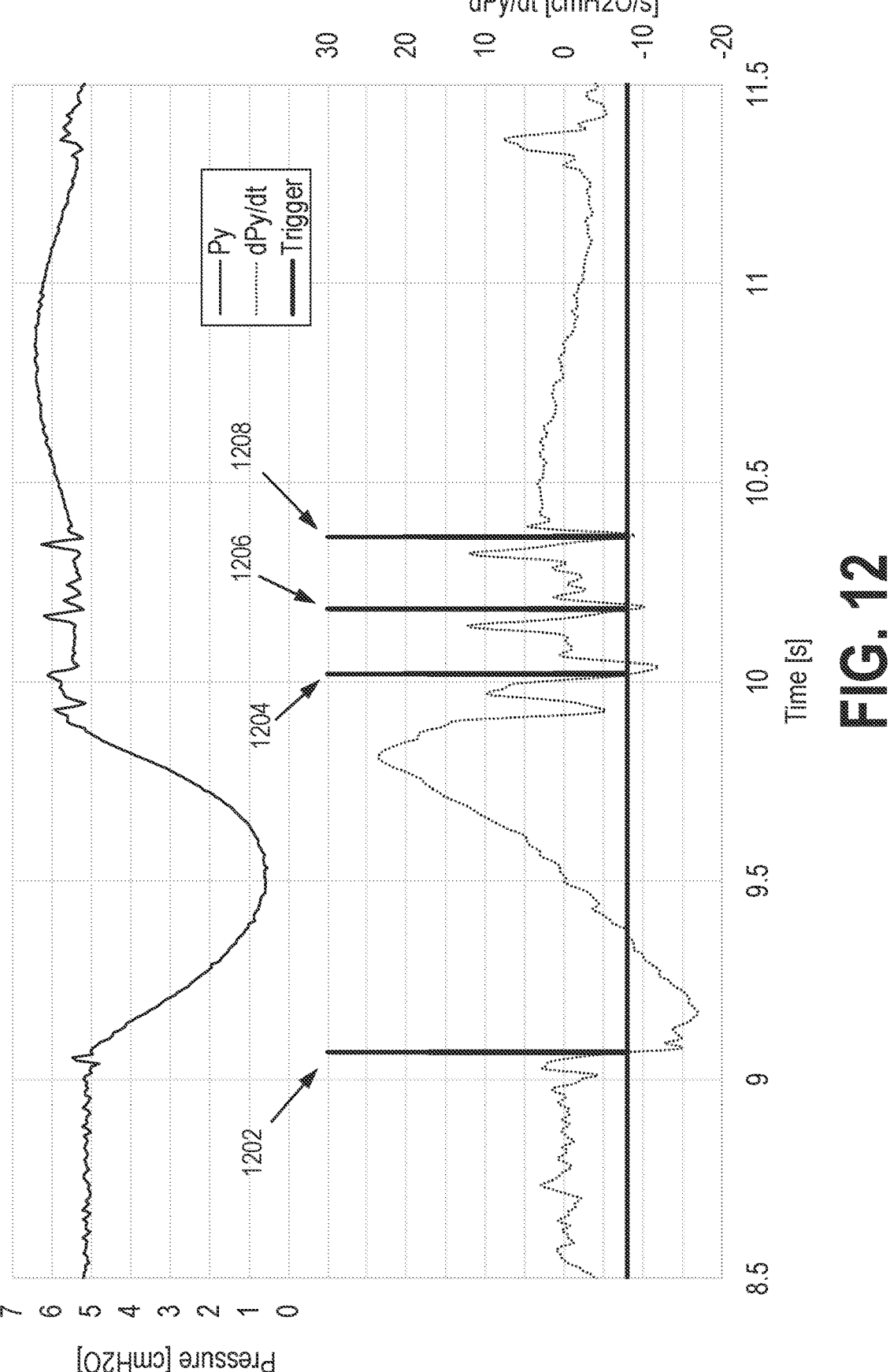
FIG. 12 is a graph illustrating one or more generated pressure triggers over the graph of FIG. 10.
Figure 13:
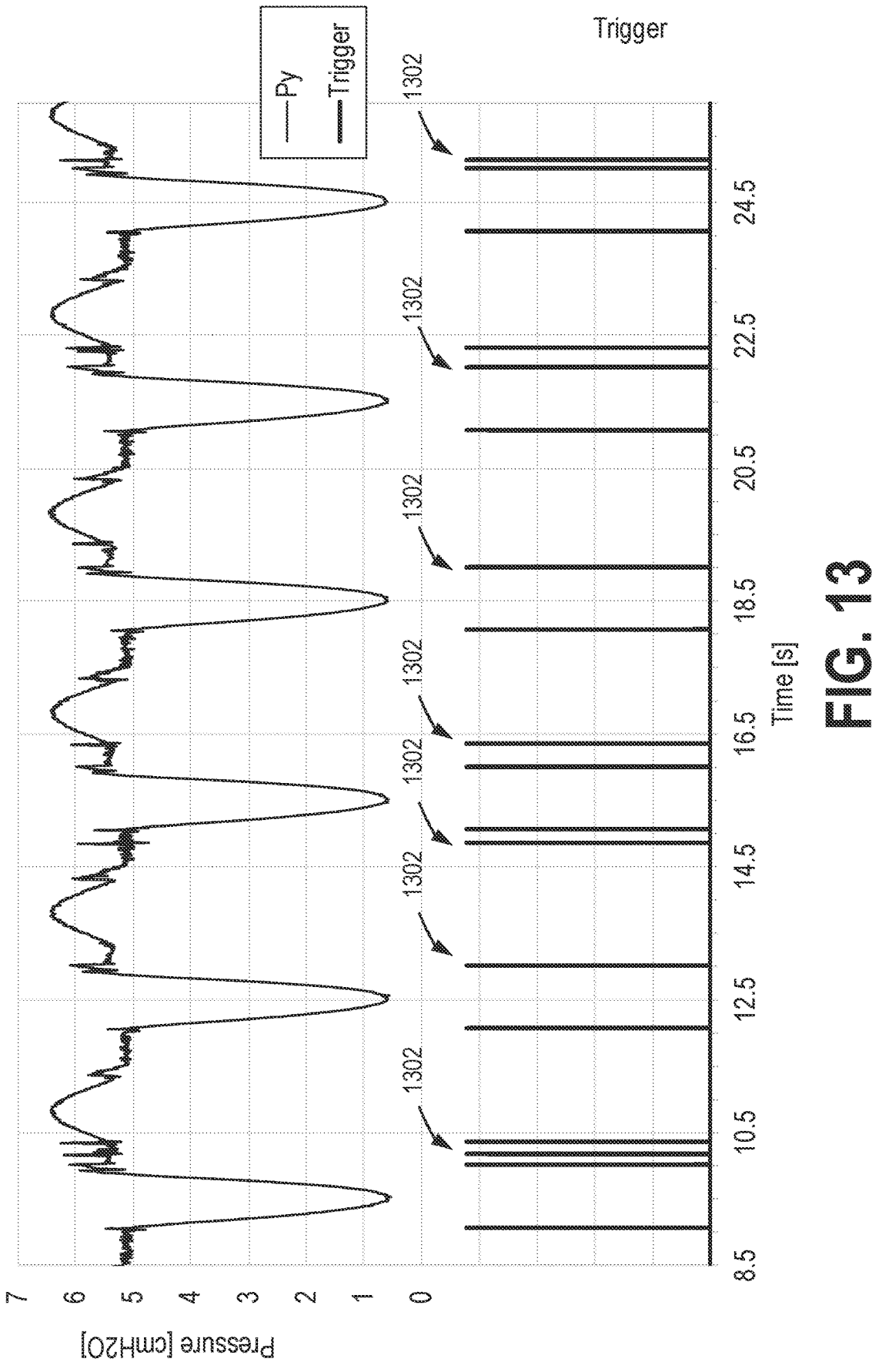
FIG. 13 is a graph illustrating one or more generated pressure triggers over a longer period of time according to aspects of the present disclosure.
Figure 14:
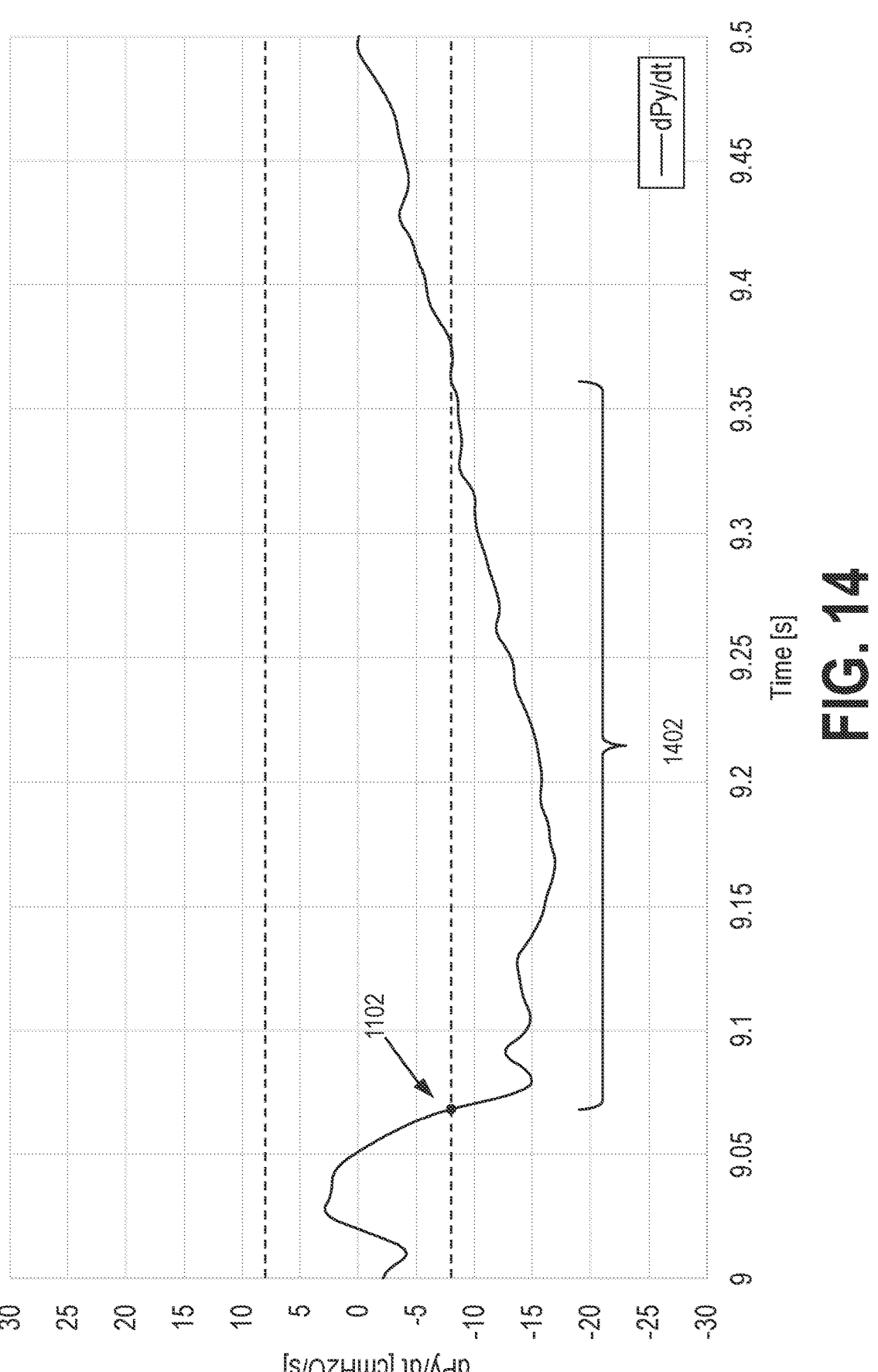
FIG. 14 is a graph illustrating a smoothed derivative signal with one or more slope limits between t=9 seconds and t=9.5 seconds.

However, as shown in FIG. 12, the four pressure triggers 1202, 1204, 1206, 1208 generated corresponding to the four points 1102, 1104, 1106, 1108 still improperly trigger pressure support after the patient's active inspiration phase (i.e., triggers 1204, 1206, and 1208) as a result of the noisy patient pressure signal (Py) 342. As shown in FIGS. 13, these false triggers 1302 accumulate significantly when viewing even a small period of time (i.e., t=8.5 seconds to t=26 seconds). At each of these points, the associated ventilator system 100 is improperly triggering delivery of a gas flow at an increased pressure contrary to the patient's actual respiratory cycle.

Figure 15:
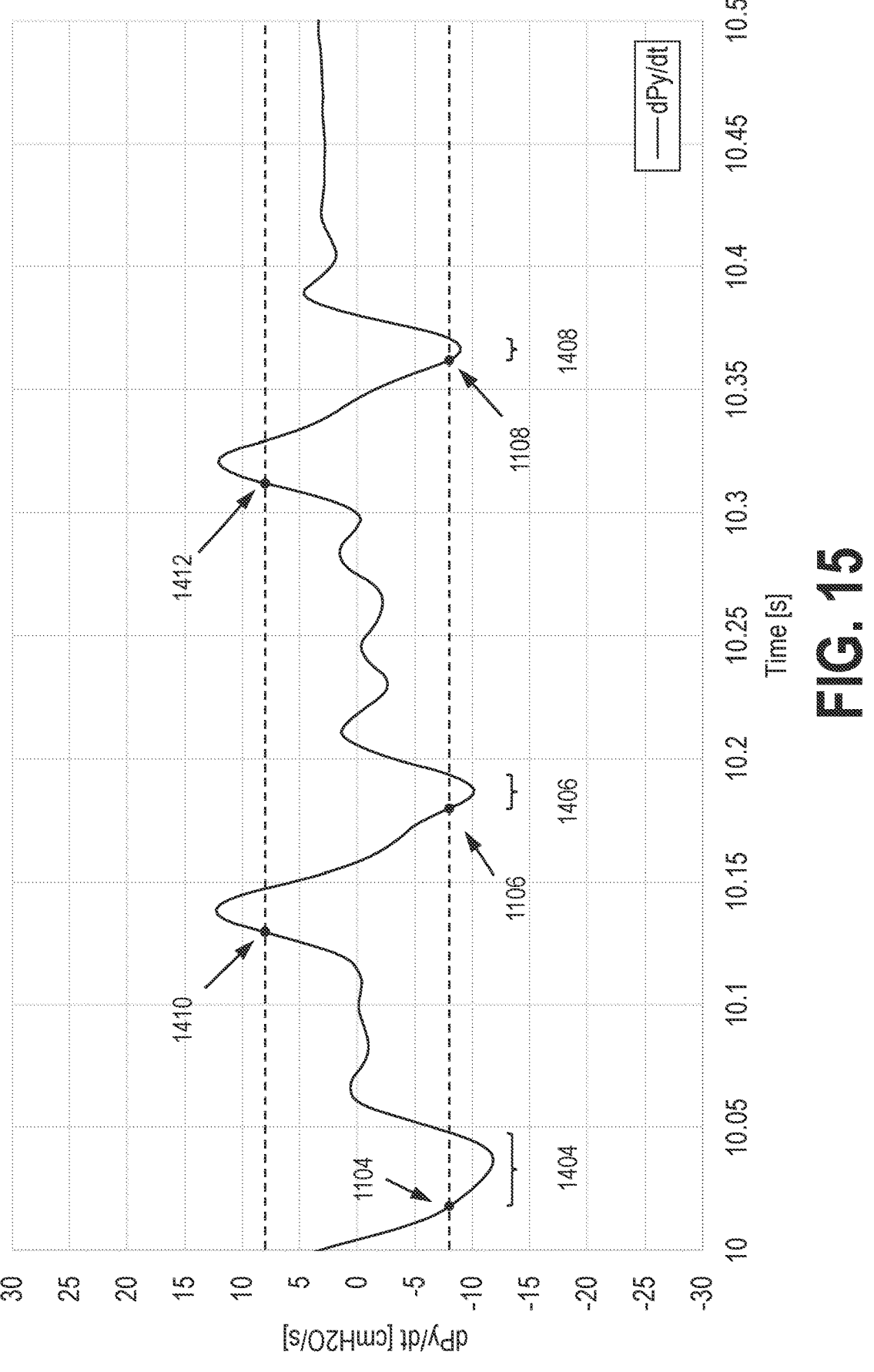
FIG. 15 is a graph illustrating a smoothed derivative signal with one or more slope limits between t=10 seconds and t=10.5 seconds.

Thus, in embodiments, the pressure controlling system 300 may apply one or more predetermined minimum inhalation durations 406 to the smoothed derivative signal (dPy/dt) 350 in order to extract the correct one or more pressure triggers 344. This step is illustrated with respect to FIG. 14 (showing the smoothed derivative signal (dPy/dt) 350 of FIG. 11 between t=9 seconds and t=9.5 seconds) and FIG. 15 (showing the smoothed derivative signal (dPy/dt) 350 of FIG. 11 between t=10 seconds and t=10.5 seconds). As shown, the crossing point 1102 is followed by a duration 1402 spanning from about 9.066 seconds to about 9.359 seconds, or about 293 milliseconds. In contrast, as shown in FIG. 15, the crossing points 1104, 1106, and 1108 are followed by a corresponding duration 1404, 1406, 1408 of about 27.3 milliseconds, about 11.7 milliseconds, and about 5.9 milliseconds, respectively.

Figure 16:
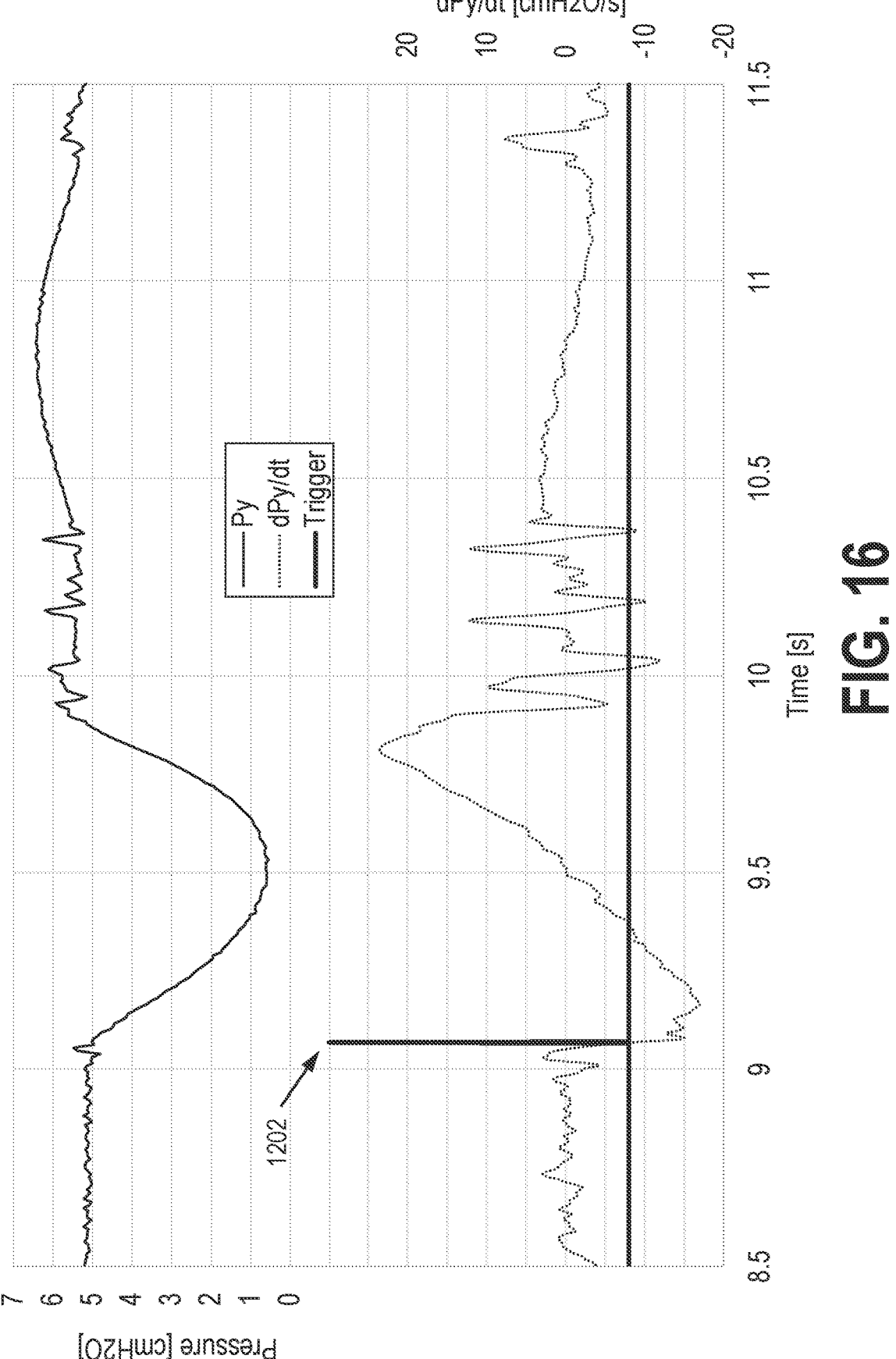
FIG. 16 is a graph illustrating one or more generated pressure triggers after applying a minimum inhalation duration according to aspects of the present disclosure.

With reference to FIG. 16, by applying one or more predetermined minimum inhalation durations 406, the improper triggers (e.g., triggers 1204, 1206, 1208) can be eliminated, leaving only the triggers (e.g., trigger 1202) that correctly correspond to the active inspiration phase of the patient's plurality of respiratory cycles. In embodiments, the minimum inhalation duration 406 may be preset by the physician and/or therapy provider, or may be determined by the pressure controlling system 300 as discussed above. In particular aspects, the minimum inhalation duration 406 can be from about 30 milliseconds to about 120 milliseconds. In the example illustrated in FIG. 16, a minimum inhalation duration of 40 milliseconds (or 20 data points taken at a resolution of Δt=2 milliseconds).

Figure 17:
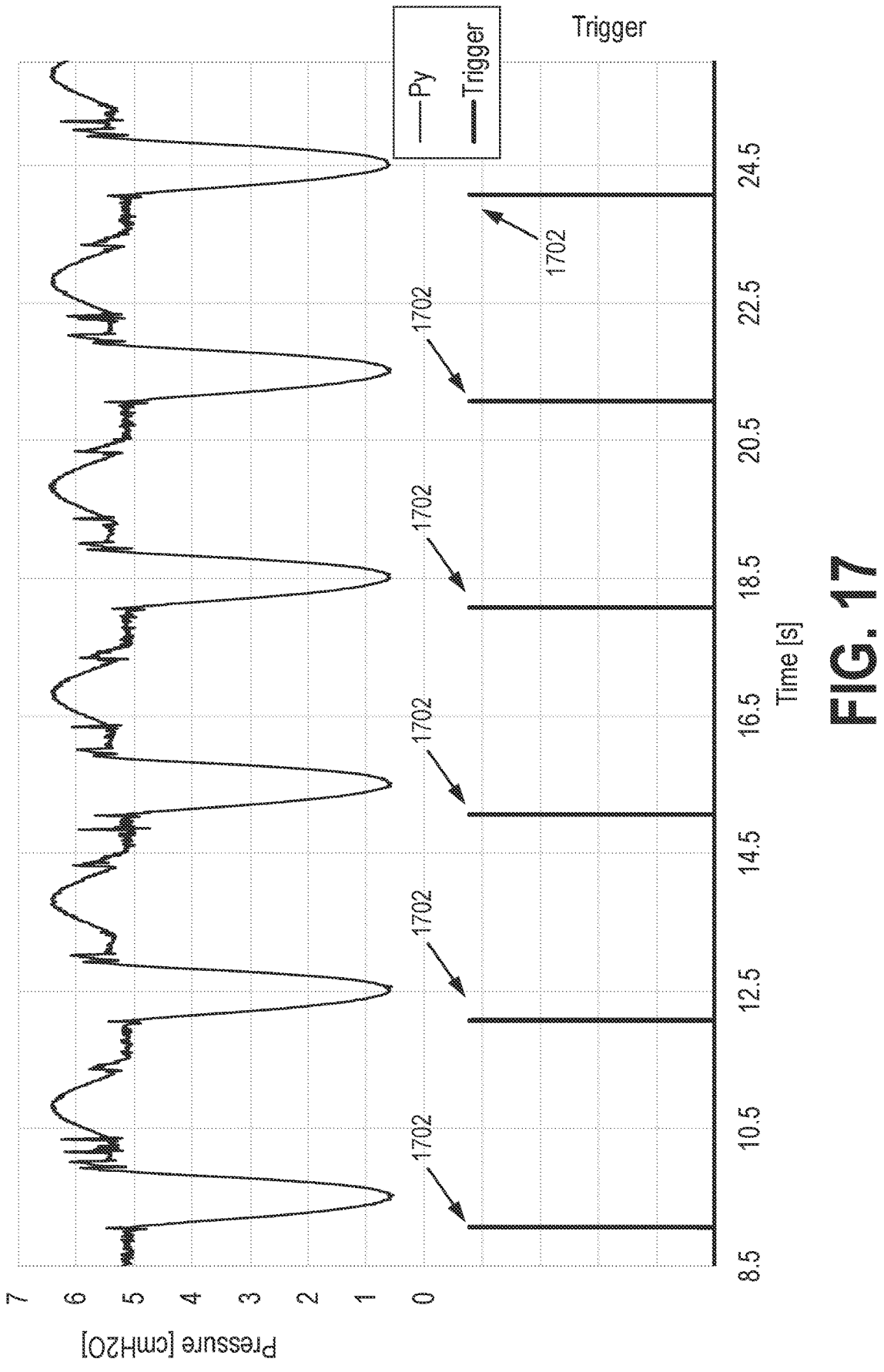
FIG. 17 is a graph illustrating a plurality of generated pressure triggers over a longer period of time after applying a minimum inhalation duration according to aspects of the present disclosure.

As shown in FIG. 17, a pressure controlling system 300 utilized in accordance with the present disclosure results in proper triggers 1702 for the simulated patient pressure signal (Py) 342 with a total trigger delay (i.e., the time between the start of inspiration and when the inspiration is detected) of less than about 500 milliseconds. In particular embodiments, the totally trigger delay according to the present disclosure can be less than about 450 milliseconds, less than about 400 milliseconds, less than about 350 milliseconds, less than about 300 milliseconds, less than about 250 milliseconds, less than about 200 milliseconds, less than about 150 milliseconds, and/or less than about 100 milliseconds.

In embodiments, it may be necessary to further apply one or more minimum peak distances 410 to the smoothed derivative signal (dPy/dt) 350 prior to extracting the one or more pressure triggers 344. In particular, if the start of an exhalation phase is detected (i.e., when the derivative signal and/or smoothed derivative signal 350 is greater than the positive predetermined slope limit 404), then a minimum distance threshold 410 may be applied by the pressure controlling system 300 to ensure that proper triggering of the respiratory support.

Figure 18:
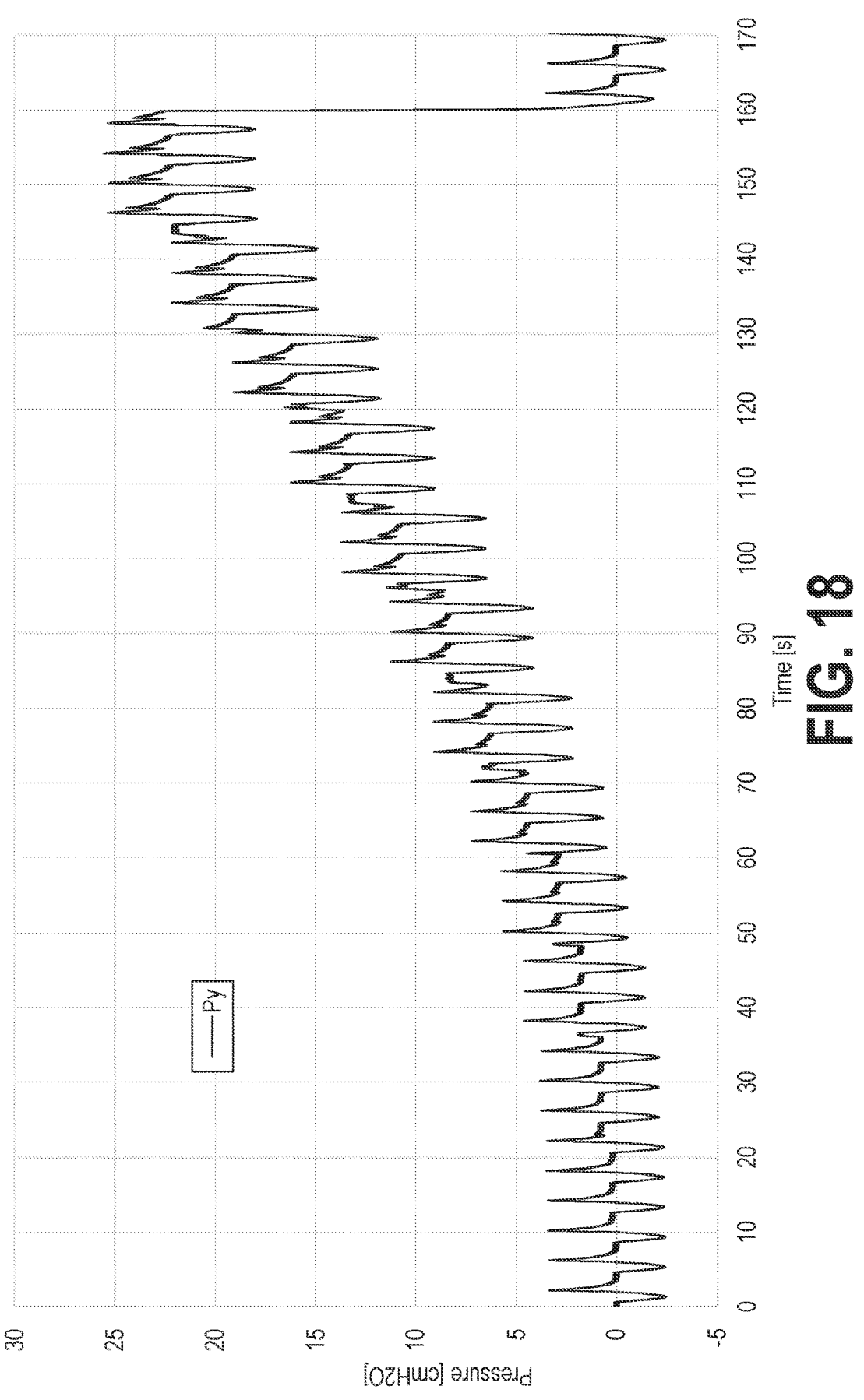
FIG. 18 is a graph illustrating a second simulated patient pressure signal over a period of time according to aspects of the present disclosure.

For example, with reference to FIGS. 18 through 24, a second simulation was performed using an ASL 5000 lung simulator with an "Adult normal" lung model at 15 breaths per minute and under "passive expiration". Further, as exemplified in FIG. 18, a stepwise increasing primary flow yielding "PEEP" pressure levels from about 0 to about 22 cmH₂O was used along with a simulated sampling rate of 5 ms (i.e., Δt=5 ms). In particular, as shown in FIG. 18, a patient pressure signal (Py) 342 was produced, and the increasing primary flow (e.g., primary flow 208) generated an upward trend in the patient pressure signal (Py) 342 until about t=160 seconds when the primary flow 208 was ceased.

As with the example shown in FIGS. 5 through 17, the pressure controlling system 300 can determine a smoothed derivative signal (dPy/dt) 350 based on the patient pressure signal (Py) 350 in order to begin extracting one or more pressure trigger moments 344. The smoothed derivative signal (dPy/dt) 350 for the patient pressure signal (Py) 350 shown in FIG. 18 is illustrated along with the corresponding patient pressure signal (Py) 350 in FIG. 19. In this example, an Lf factor of 16 was used to determine the smoothed derivative signal (dPy/dt) 350.

Figure 20:
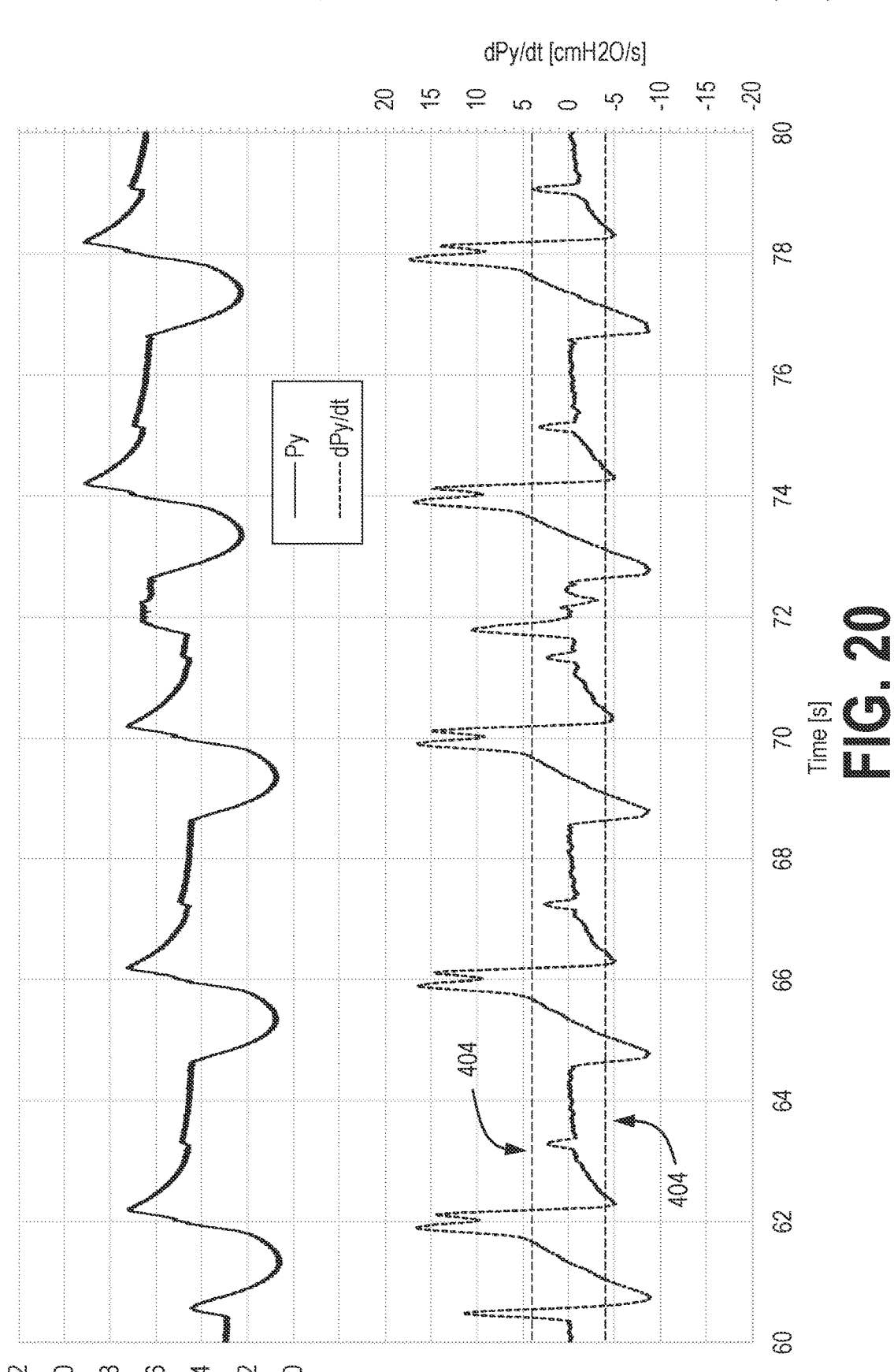
FIG. 20 is a graph illustrating a portion of the smoothed derivative signal from FIG. 19 with one or more slope limits according to aspects of the present disclosure.
Figure 21:
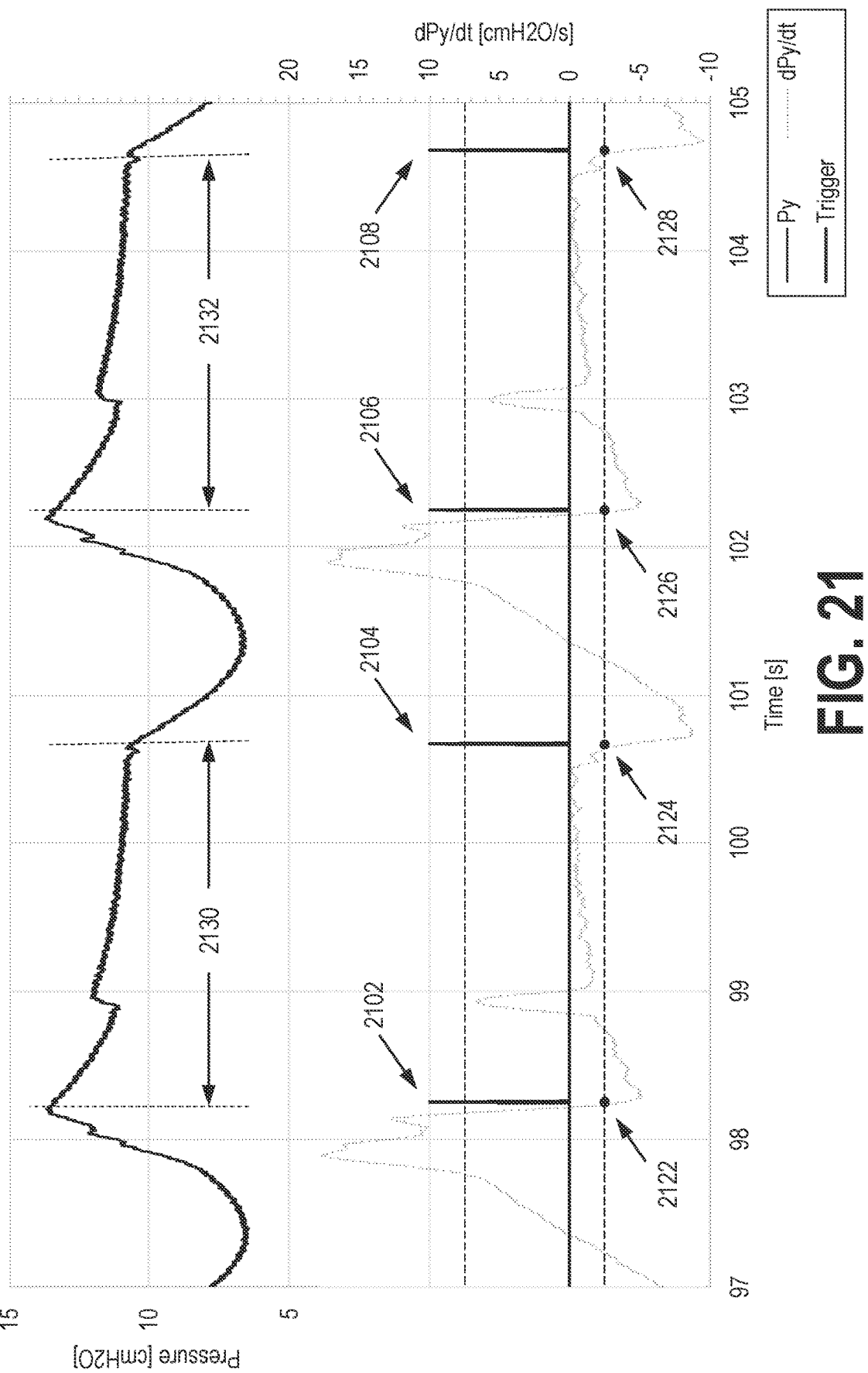
FIG. 21 is a graph illustrating a portion of the patient pressure signal and the smoothed derivative signal from FIG. 19 with one or more slope limits and extracted pressure triggers according to aspects of the present disclosure.
Figure 22:
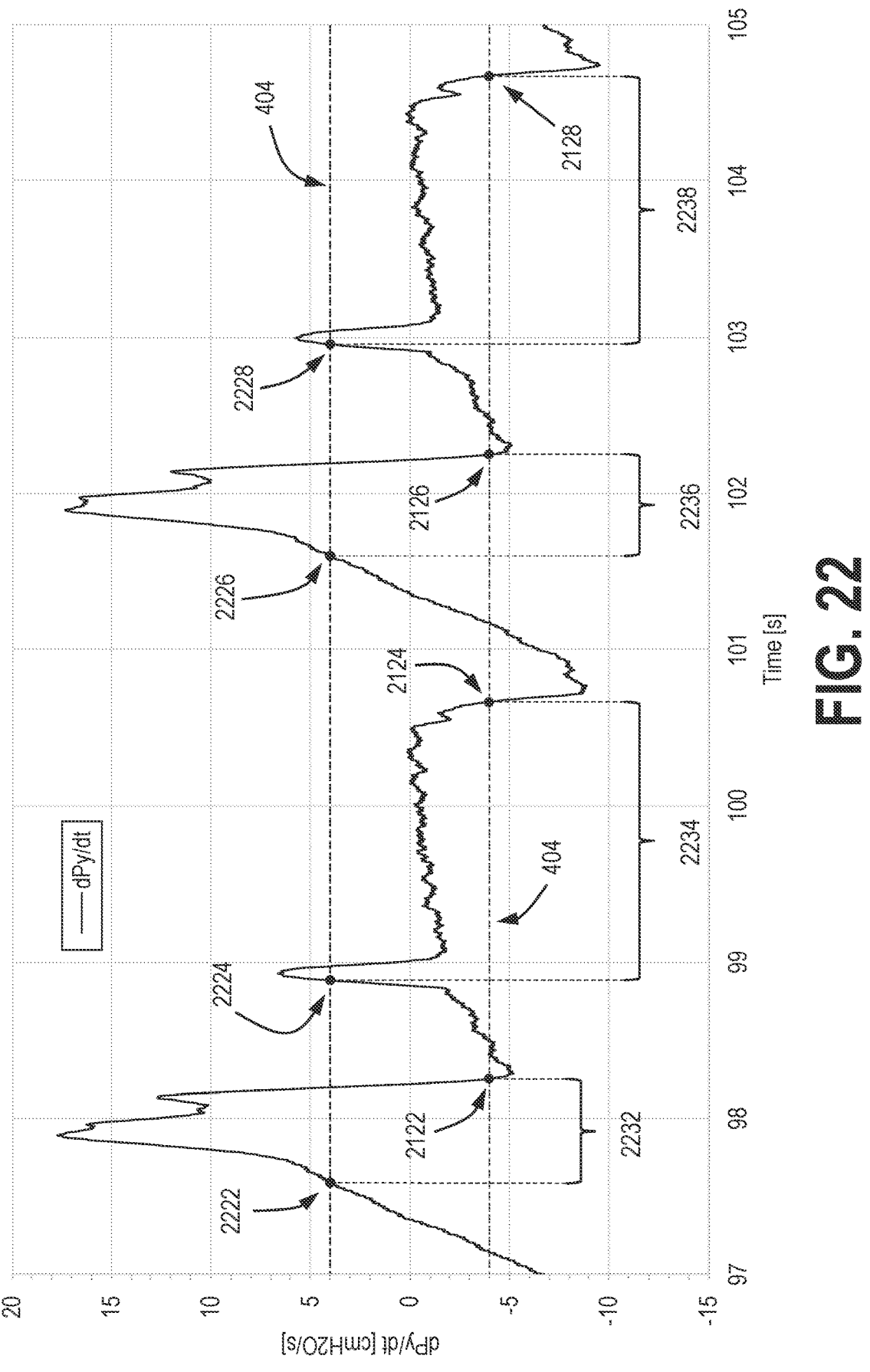
FIG. 22 is a graph illustrating the smoothed derivative signal from FIG. 21 according to aspects of the present disclosure.

Then, with reference to FIGS. 20 and 21, the pressure controlling system 300 can apply one or more slope limits 404 and a minimum inhalation duration 406 to the smoothed derivative signal (dPy/dt) 350. This results in one or more pressure trigger moments 344 (e.g., pressure triggers 2102, 2104, 2106, 2108) being produced. As shown in FIG. 21, the trigger moments 2102, 2104, 2106, 2108 correspond to points 2122, 2124, 2126, 2128 when the smoothed derivative signal (dPy/dt) 350 transitions from being greater than the negative slope limit 404 to being less than the negative slope limit 404. Here, the slope limits 404 are ±4 cmH₂O/s and the minimum inhalation duration is at least 100 milliseconds. However, as seen in FIG. 21, pressure trigger moments 2102, 2106 are incorrectly produced despite the patient pressure signal (Py) 342 indicating that the patient is in an exhalation phase 2130, 2132. Thus, in embodiments, a minimum peak distance 410 may be applied by the pressure controlling system 300 to ensure proper triggering of the ventilation system 100.

Figure 19:
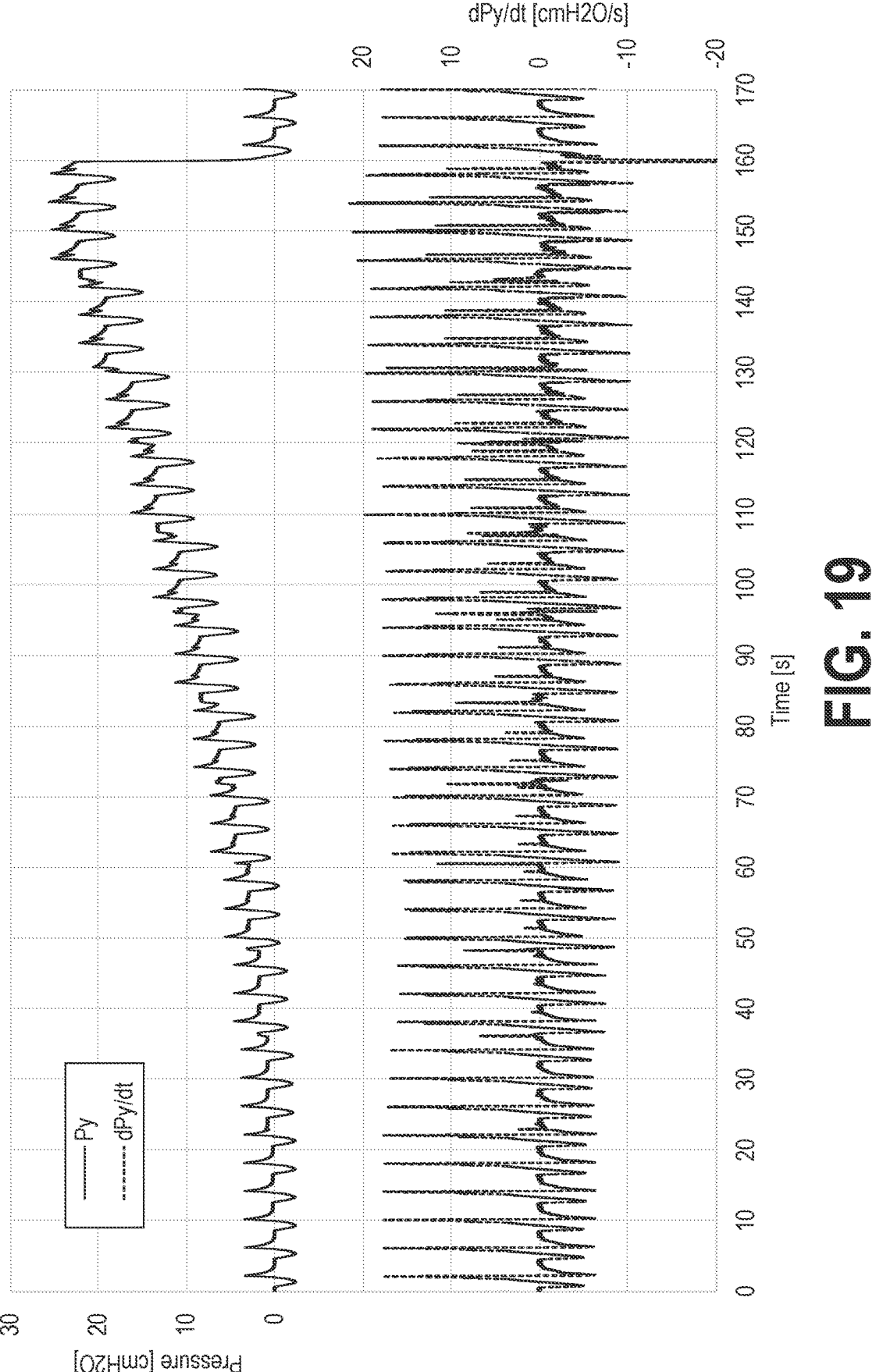
FIG. 19 is a graph illustrating the patient pressure signal of FIG. 18 and a smoothed derivative signal according to aspects of the present disclosure.

In embodiments, a minimum peak distance 410 may be defined as the distance between a trigger moment and a previous positive peak where the smoothed derivative signal (dPy/dt) 350 was greater than the positive slope limit. For example, with reference to FIG. 22, the smoothed derivative signal (dPy/dt) 350 shown in FIGS. 19-21 are illustrated. The points 2122, 2124, 2126, 2128 where the smoothed derivative signal (dPy/dt) 350 drops below the negative slope limit 404 (i.e., –4 cmH₂O/s) are indicated along with the points 2222, 2224, 2226, 2228 where the smoothed derivative signal (dPy/dt) 350 rises above the positive slope limit 404 (i.e., +4 cmH₂O/s). According to a minimum peak distance 410 determination, each potential pressure trigger moment 2122, 2124, 2126, 2128 can be compared with the moment immediately preceding it when the smoothed derivative signal (dPy/dt) 350 exceeds the positive slope limit 404. As shown in the table below, applying a minimum peak distance 410 to the points 2122, 2124, 2126, and 2128 correctly extracts the points 2124, 2128, which correspond to inspiration phases of the patient's respiratory cycle according to the patient pressure signal (Py) 342:

TABLE 1

| Applying Minimum Peak Distance of 1.5 seconds | | | |
| --- | --- | --- | --- |
| | Trigger Point Timing [s] | Preceding Peak Timing [s] | Trigger-Peak Distance [s] | Meets minimum peak distance? |
| Trigger Point #1 | 98.25 | 97.59 | 0.66 | No |
| Trigger Point #2 | 100.67 | 98.885 | 1.785 | Yes |
| Trigger Point #3 | 102.25 | 101.605 | 0.645 | No |
| Trigger Point #4 | 104.68 | 102.96 | 1.72 | Yes |

Figure 23:
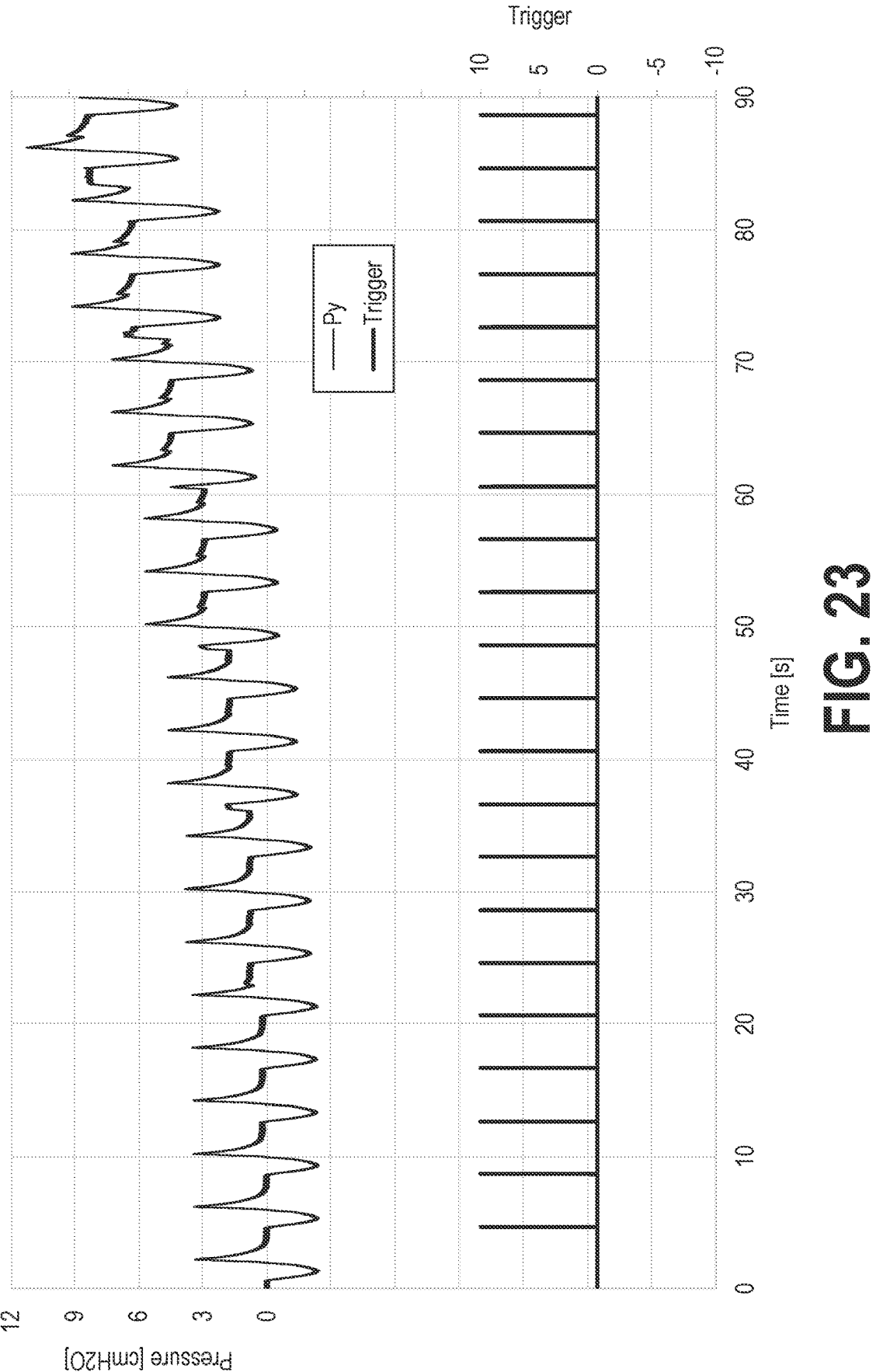
FIG. 23 is a graph illustrating the patient pressure signal from FIG. 18 and the corresponding pressure triggers from t=0 seconds to t=90 seconds according to aspects of the present disclosure.
Figure 24:
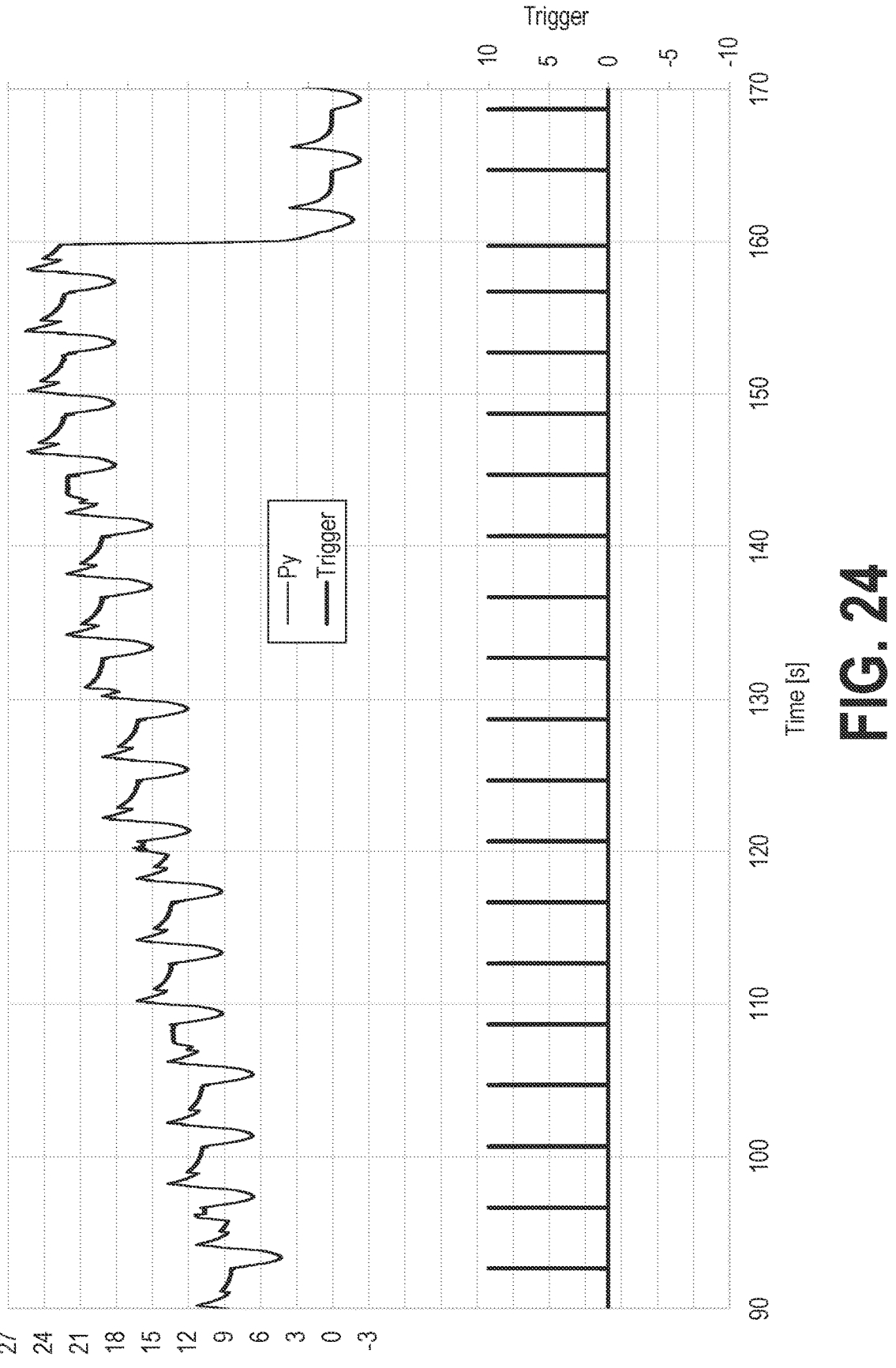
FIG. 24 is a graph illustrating the patient pressure signal from FIG. 19 and the corresponding pressure triggers from t=90 seconds to t=170 seconds according to aspects of the present disclosure.

Accordingly, the distances 2232, 2236 do not meet the minimum peak distance 410, while the distances 2234, 2236 satisfy the minimum peak distance 410 requirement. As shown in FIGS. 23 and 24, the one or more trigger moments

344 extracted based on the smoothed derivative signal (dPy/dt) 350 now properly correspond to each of the inhalation phases of the patient's respiratory cycles.

In embodiments, the minimum peak distance 410 may be preset by a physician and/or therapy provider. In further aspects, the minimum peak distance 410 may be determined by the pressure controlling system 300 based on, for example and without limitation, the previous breathing cycle for the patient. In an aspect, the minimum peak distance 410 from about 0.5 seconds to about 2 seconds, including from about 0.5 seconds to about 0.75 seconds, from about 0.75 seconds to about 1.0 seconds, from about 1.0 seconds to about 1.25 seconds, from about 1.25 seconds to about 1.5 seconds, from about 1.5 seconds to about 1.75 seconds, from about 1.75 seconds to about 2.0 seconds, and any combination of endpoints thereof.

Returning to FIG. 1, the ventilation system 100 can be a wearable ventilator with a portable gas source(s) 110A, 110B. A ventilator module 116 may include or be in communication with one or more other functional accessories. For example, the control system 102 may include an interface bus (e.g., interface bus 306 shown in FIG. 3) that is adapted to transmit information regarding the patient, the patient's therapy, and the performance of the ventilation system 100 to a remote location for review, analysis, remote intervention, two-way communication, and/or archiving. In an aspect, the patient's compliance with the therapy and/or utilization of the therapy can be monitored and assessed. In a further aspect, important information can be extracted and analyzed, including the patient's breathing rate, I:E ratio, oxygen usage, activity level, depth of breathing, and the like. In still further aspects, the ventilator module 116 can receive information from an external source, such as programming instructions for setting titration options for the ventilator output to meet the needs of the patient or for sending instructions to the patient.

In embodiments, the oxygen source 110A and/or compressed air source 110B can be included, typically externally, to the ventilator module 116. In other embodiments, the oxygen source 110A and/or the compressed air source 110B can be internal to the ventilator module 116, for example, if the therapy is being used for stationary use (in a home, hospital, outpatient facility, etc.). A gas blender 118 can be included to control the fractional O₂ delivered to the gas delivery lines 108. One or more sensors may be included in a sensor suite 120, including but not limited to, a pulse oximeter adapted to titrate settings of the ventilator module 116 to meet the physiological needs of the patient (e.g., setting the correct oxygen blender 118 settings or ventilator volume output), a pedometer, a CO₂ sensor, and/or the like. The ventilation system 100 can also include a drug delivery system 122, an air conditioner 124 (e.g., humidifier and/or dehumidifier), a flow regulator 126, a pressure regulator 128, a filtration system 130, and/or a user interface 132. One or more of these components 118, 120, 122, 124, 126, 128, 130, 132 may be internal or external to the ventilator module 116.

In an aspect, the drug delivery system 122 can be adapted to propel and/or deposit aerosolized drug delivery pharmacologics deep within the respiratory system 104 of the patient without a carrier propellant.

In an aspect, the user interface 132 can include a display screen adapted to display information regarding the therapy provided by the ventilation system 100, including one or more settings, and can be adapted to receive user input that may be used by the control system 102 (e.g., to control one or more settings of the ventilation system 100 and/or ventilator module 116).

Also provided herein are methods of controlling a ventilation system 100 attached to a patient. With reference to FIGS. 25A and 25B, one such method 2500 is illustrated according to aspects of the present disclosure.

In a step 2502, the method 2500 can include supplying a gas mixture 208 to the patient (i.e., the patient's airways 104) via a pressure support device 100. The gas mixture 208 may be delivered to the patient at a first pressure level via a patient airway interface 106 and a gas flow path 112 of the ventilation system 100.

In a step 2504, the method 2500 can include taking measurements (e.g., real-time measurements) of the patient's breathing using a pressure sensor 114. In embodiments, the measurements can be a patient pressure signal (Py) 342. In an aspect, the patient pressure sensor 114 can be disposed along the gas flow path 112 as described above.

In a step 2506, the method 2500 can include receiving the patient pressure signal (Py) 342 for the patient. In embodiments, patient pressure signal (Py) 342 may be received by the control system 102 of the ventilation system 100 and/or by a pressure trigger module 328 of a pressure controlling system 300. In an aspect, the pressure trigger module 328 may be integrated into the control system 102 such that the ventilation system 100 comprises the pressure controlling system 300.

In a step 2508, the method 2500 can optionally include determining at least one smoothing coefficient 402 for the patient. Alternatively, one or more smoothing coefficients 402 may be preset by a physician and/or therapy provider.

In steps 2510 and 2512, the method 2500 can include determining a derivative signal (dPy/dt) 350 based on the patient pressure signal (Py) 342 and applying the smoothing coefficient(s) 402 to the derivative signal (dPy/dt) 350 and/or the patient pressure signal (Py) 342. In specific embodiments, steps 2510 and 2512 may be performed simultaneously. That is, the derivative signal (dPy/dt) 350 may be determined and smoothed at the same time.

In steps 2514, 2516, and 2518, the method 2500 can optionally include determining one or more slope limits 404, one or more minimum inhalation durations 406, and one or more minimum peak distances 410 for the patient, as described above. Alternatively, one or more of these process variables 352 may be preset by a physician and/or therapy provider in order to meet the physiological needs of the patient.

In step 2520 and 2522, the method 2500 can include applying one or more of the process variables 352 to the smoothed derivative signal (dPy/dt) 350 in order to extract one or more pressure triggers 344. In an aspect, the one or more pressure triggers 344 indicate an active inspiration phase of the patient's breathing.

In a step 2524, the method 2500 can include modifying the delivery of the gas flow 208. If the pressure controlling system 300 is external to the ventilation system 100, it may be necessary (in step 2524) to provide an instruction to the ventilation system 100 to modify the pressure level of the gas mixture 208 being delivered to the patient. As used herein, the term "instruction" refers to a digital signal containing data (e.g., pressure triggers 344) in a format that allows the ventilation system 100 to know at least when to deliver or modify the pressure level of the gas flow 208. In embodiments, the pressure level may be modified by increasing the pressure level from a first pressure level 348 (i.e., a lower PEEP pressure level) to a second pressure level

346 (i.e., a higher IPAP pressure level). In an aspect, the second pressure level 346 may be maintained by the ventilation system 100 for a period of time corresponding to the patient's inspiratory phase. In other words, once the patient begins an exhalation phase, the pressure level of the gas flow 208 is reduced back to the first pressure level 348 and/or another pressure level lower than the second pressure level 346.

As described herein, the patient pressure signal (Py) 342 may be received continuously from the patient pressure sensor 114 over a plurality of respiratory cycles of the patient, the one or more pressure triggers 344 may be generated for each active inspiration phase of the plurality of respiratory cycles of the patient, and the gas mixture 208 may be delivered to the patient at the higher inspiratory positive airway pressure 346 for the period of time with a trigger delay of less than 500 milliseconds after the start of each active inspiration phase of the plurality of respiratory cycles of the patient.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

The above-described examples of the described subject matter can be implemented in any of numerous ways. For example, some aspects can be implemented using hardware, software or a combination thereof. When any aspect is implemented at least in part in software, the software code can be executed on any suitable processor or collection of processors, whether provided in a single device or computer or distributed among multiple devices/computers.

The present disclosure can be implemented as a system, a method, and/or a computer program product at any possible technical detail level of integration. The computer program product can include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium comprises the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, comprising an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, comprising a local area network (LAN) or a wide area network (WAN), or the connection can be made to an external computer (for example, through the Internet using an Internet Service Provider). In some examples, electronic circuitry comprising, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions can be provided to a processor of a, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture comprising instructions which implement aspects of the function/act specified in the flowchart and/or block diagram or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow-chart and/or block diagram block or blocks.

The flowchart and block diagrams in the Figures illustrate the architecture, functionality, and operation of possible implementations of systems, methods, and computer programs products according to various examples of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other implementations are within the scope of the following claims and other claims to which the applicant can be entitled.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for controlling a pressure level of a gas mixture being delivered to a patient, the system comprising:
  one or more processors in communication with a ventilation system; and
  a memory storing instructions that, when executed by the one or more processors, cause system to perform the following:
    receive, from a pressure sensor of the ventilation system, a patient pressure signal;

generate one or more pressure triggers by:
      determining a derivative signal based on the patient pressure signal;
      determining a smoothed derivative signal based on the patient pressure signal and/or the derivative signal by applying a predetermined smoothing coefficient; and
      extracting the one or more pressure triggers based on the smoothed derivative signal by applying a predetermined slope limit, a predetermined minimum inhalation duration, and/or a predetermined minimum peak distance to the smoothed derivative signal, wherein the one or more pressure triggers indicate an active inspiration phase of the patient's breathing; and
    provide an instruction to the ventilation system to modify the pressure level of the gas mixture being delivered to the patient based on the one or more pressure triggers.

2. The system of claim 1, wherein each of the one or more pressure triggers corresponds to a time when the smoothed derivative signal drops below the predetermined slope limit and remains below the predetermined slope limit for at least the predetermined minimum inhalation duration.

3. A method of controlling a ventilation system attached to a patient, the method comprising:
  delivering a gas mixture to the patient at a first pressure level via a patient airway interface and a gas flow path of the ventilation system;
  receiving a patient pressure signal for the patient using a patient pressure sensor located along the gas flow path in proximity to a negative pressure area generated by delivery of the gas mixture;
  generate one or more pressure triggers by:
    determining a derivative signal based on the patient pressure signal;
    determining a smoothed derivative signal by applying a predetermined smoothing coefficient to the patient pressure signal and/or the derivative signal; and
    extracting one or more pressure triggers based on the smoothed derivative signal by applying a predetermined slope limit, a predetermined minimum inhalation duration, and/or a predetermined minimum peak distance to the smoothed derivative signal, wherein each pressure trigger corresponds to an active inspiration phase of the patient's breathing;
  modifying the pressure level of the gas mixture being delivered to the patient for a period of time based on the one or more pressure triggers, wherein the pressure level is modified by increasing the pressure level of the gas mixture being delivered to the patient from the first pressure level to a higher inspiratory positive airway pressure for the period of time.

4. The method of claim 3, wherein the patient pressure signal is received continuously from the patient pressure sensor over a plurality of respiratory cycles of the patient, the one or more pressure triggers are generated for each active inspiration phase of the plurality of respiratory cycles of the patient, and delivery of the gas mixture is modified within 500 milliseconds of each active inspiration phase of the plurality of respiratory cycles of the patient.

* * * * *